United States Patent
Kodama et al.

(10) Patent No.: US 7,135,473 B2
(45) Date of Patent: Nov. 14, 2006

(54) CYCLIC DIAMINE COMPOUND WITH CONDENSED-RING GROUPS

(75) Inventors: Tatsuhiko Kodama, Tokyo (JP); Masahiro Tamura, Tokyo (JP); Toshiaki Oda, Tokyo (JP); Yukiyoshi Yamazaki, Tokyo (JP); Masahiro Nishikawa, Tokyo (JP); Takeshi Doi, Tokyo (JP); Yoshinori Kyotani, Tokyo (JP)

(73) Assignee: Kowa Co., Ltd., Nagoya (JP)

( * ) Notice: Subject to any disclaimer, the term of this patent is extended or adjusted under 35 U.S.C. 154(b) by 339 days.

(21) Appl. No.: 10/639,457

(22) Filed: Aug. 13, 2003

(65) Prior Publication Data

US 2004/0058913 A1 Mar. 25, 2004

Related U.S. Application Data

(62) Division of application No. 09/893,696, filed on Jun. 29, 2001, now Pat. No. 6,632,810.

(51) Int. Cl.
*A61K 31/497* (2006.01)
*A61P 37/00* (2006.01)
*C07D 239/00* (2006.01)
*C07D 401/00* (2006.01)
*C07D 403/00* (2006.01)

(52) U.S. Cl. .......................... 514/252.13; 514/252.17; 514/253.06; 514/254.02; 514/254.06; 514/254.09; 514/254.11; 514/255.04; 544/283; 544/363; 544/368; 544/370; 544/373; 544/376; 544/398

(58) Field of Classification Search ........... 514/252.13, 514/252.17, 253.06, 254.02, 254.06, 254.09, 514/254.11, 255.04; 544/283, 363, 368, 544/370, 373, 376, 398
See application file for complete search history.

(56) References Cited

U.S. PATENT DOCUMENTS

| 6,432,957 | B1 | 8/2002 | Kodama et al. | ....... 514/252.13 |
| 6,472,386 | B1 | 10/2002 | Kodama et al. | ....... 514/211.08 |
| 6,509,329 | B1 | 1/2003 | Kodama et al. | ....... 514/212.01 |
| 6,552,188 | B1 | 4/2003 | Kodama et al. | ............ 540/575 |

FOREIGN PATENT DOCUMENTS

| JP | 9-143075 | 6/1997 |
| JP | 10-67656 | 3/1998 |
| JP | 10-147568 | 6/1998 |
| JP | 10-182550 | 7/1998 |
| JP | 11-92382 | 4/1999 |
| JP | 2000-86641 | 3/2000 |
| JP | 2000-509070 | 7/2000 |
| JP | 2000-319277 | 11/2000 |

OTHER PUBLICATIONS

Y. Ohkawara, et al., "*In Situ* Expression of the Cell Adhesion Molecules in Bronchial Tissues Form Asthmatics With Air Flow Limitation: *In Vivo* Evidence of VCAM-1/VLA-4 Interaction in Selective Eosinophil Infiltration", *American Journal of Respiratory Cell and Molecular Biology*, 1995, vol. 12, pp. 4-12.

A. Sakai, et al., "P-Selectin and Vascular Cell Adhesion Molecule-1 are Focally Expressed in Aortas of Hypercholesterolemic Rabbits Before Intimal Accumulation of Macrophages and T Lymphocytes", *Arteriosclerosis, Thrombosis, and Vascular Biology*, Feb. 1997, vol. 17, No. 2, pp. 310-316.

H. Wakita, et al., "E-Selectin and Vascular Cell Adhesion Molecule-1 as Critical Adhesion Molecules for Infiltration of T Lymphocytes and Eosinophils in Atopic Dermatitis", *Journal of Cutaneous Pathology*, 1994, pp. 33-39.

T. Satoh, et al., "Cyclophosphamide-Induced Blood and Tissue Eosinophilia in Contact Sensitivity: Mechanism of Hapten-Induced Eosinophil Recruitment Into the Skin", *European Journal of Immunology*, 1997, vol. 27, pp. 85-91.

P. P. Tak, et al., "Expression of Adhesion Molecules in Early Rheumatoid Synovial Tissue", *Clinical Immunology and Immunopathology*, Dec. 1995, vol. 77, No. 3, pp. 236-242.

S. Albelda, et al., "Adhesion Molecules and Inflammatory Injury", *The FASEB Journal*, Reviews, May 1994, vol. 8, pp. 504-512.

T. A. Springer, "Traffic Signals on Endothelium for Lymphocyte Recirculation and Leukocyte Emigration", *Annu. Rev. Physiol.*, 1995, vol. 57, pp. 827-872.

(Continued)

*Primary Examiner*—Brenda Coleman
(74) *Attorney, Agent, or Firm*—Oblon, Spivak, McClelland, Maier & Neustadt, P.C.

(57) ABSTRACT

A cyclic diamine compound of formula (1):

wherein $R^1$ and $R^2$ are individually a hydrogen atom or a methoxy group, provided $R^1$ is a methoxy group when $R^2$ is a hydrogen atom, or a hydrogen atom when $R^2$ is a methoxy group; A is an oxygen atom, a sulfur atom, CH=CH, CH=N or $NR^3$, in which $R^3$ is a hydrogen atom, or a lower alkyl, hydroxy lower alkyl, lower alkoxy lower alkyl, aryl or aryl lower alkyl group; B is a nitrogen atom, CH or $CR^4$, in which $R^4$ is a hydrogen atom, or a lower alkyl, hydroxy lower alkyl, lower alkoxy lower alkyl, aryl or aryl lower alkyl group; m is 1 or 2; and n is a number of 1 to 5, an acid-addition salt thereof, or a hydrate thereof. The compound has inhibitory effects on cell adhesion and is useful for treatment of allergy, asthma, rheumatism, arteriosclerosis, and inflammation.

10 Claims, No Drawings

OTHER PUBLICATIONS

S. A. Michie, et al., "The Roles of α4-Integrins in the Development of Insulin—Dependent Diabetes Mellitus", *Curr. Top. Microbiol. Immunol.*, 1998, vol. 231, pp. 65-83.

N. Ebihara, et al., "Anti VLA-4 Monoclonal Antibody Inhibits Eosinophil Infiltration in Allergic Conjunctivitis Model of Guinea Pig", *Current Eve Research*, 1999, vol. 19, No. 1, pp. 20-25.

S. M. Whitcup, et al., "Blocking ICAM-1 (CD54) and LFA-1 (CD11a) Inhibits Experimental Allergic Conjunctivitis", *Clinical Immunology*, Nov. 1999, vol. 93, No. 2, pp. 107-113.

A. Soriano, et al., "VCAM-1, but not ICAM-1 or MAdCam-1, Immunoblockade Ameliorates DSS-Induced Colitis in Mice", *Laboratory Investigation*, Oct. 2000, vol. 80, No. 10, pp. 1541-1551.

A. Zeidler, et al., "Therapeutic Effects of Antibodies Against Adhesion Molecules in Murine Collagen Type II-Induced Arthritis", *Autoimmunity*, 1995, vol. 21, pp. 245-252.

F. Bendjelloul, et al., "Intercellular Adhesion Molecule-1 (ICAM-1) Deficiency Protects Mice Against Severe Forms of Experimentally Induced Colitis", *Clinical and Experimental Immunology*, 2000, vol. 119, pp. 57-63.

W. W. Wolyniec, et al., "Reduction of Antigen-Induced Airway Hyperreactivity and Eosinophilia in ICAM-1-Deficient Mice", *American Journal of Respiratory Cell and Molecular Biology*, 1998, vol. 18, pp. 777-785.

D. C. Bullard, et al., "Reduced Susceptibility to Collagen-Induced Arthritis in Mice Deficient in Intercellular Adhesion Molecule-1", *The Journal of Immunology*, 1996, vol. 157, pp. 3153-3158.

D. H. Boschelli, et al., "Inhibition of E-Selection-, ICAM-1-, and VCAM-1-Mediated Cell Adhesion by Benzo(b)Thiophene-, Benzofuran-, Indole-, and Naphthalene-2-Carboxamides: Identification of PD 144795 as an Antinflammtory Agent", *Journal of Medicinal Chemistry*, 1995, vol. 38, No. 22, pp. 4597-4614.

CYCLIC DIAMINE COMPOUND WITH CONDENSED-RING GROUPS

CROSS-REFERENCE TO A RELATED APPLICATION

The present application is a divisional application of U.S. Ser. No. 09/893,696 filed Jun. 29, 2001, which has been allowed now U.S. Pat. No. 6,632,810.

BACKGROUND OF THE INVENTION

1. Field of the Invention

The present invention relates to novel cyclic diamine compounds which have inhibitory effects on both cell adhesion and cell infiltration and are useful as anti-asthmatic agents, anti-allergic agents, anti-rheumatic agents, anti-arteriosclerotic agents, anti-inflammatory agents or the like, and medicines containing such compounds.

2. Description of the Background Art

In various inflammatory diseases, infiltration of leukocytes into inflammatory sites is observed. For example, infiltration of eosinophils into the bronchus in asthma (Ohkawara, Y. et al., Am. J. Respir. Cell Mol. Biol., 12, 4–12 (1995)), infiltration of macrophages and T lymphocytes into the aorta in arteriosclerosis (Sakai, A. et al., Arterioscler Thromb. Vasc. Biol., 17, 310–316 (1997)), infiltration of T lymphocytes and eosinophils into the skin in atopic dermatitis (Wakita H. et al., J. Cutan. Pathol., 21, 33–39 (1994)) or contact dermatitis (Satoh, T. et al., Eur. J. Immunol., 27, 85–91 (1997)), and infiltration of various leukocytes into rheumatoid synovial tissue (Tak, P P. et al., Clin. Immunol. Immunopathol., 77, 236–242 (1995)), have been reported.

Infiltration of these leukocytes is elicited by cytokines, chemokines, lipids, and complements produced in inflammatory sites (Albelda, S M. et al., FASEB J., 8, 504–512 (1994)). Activated leukocytes adhere to vascular endothelial cells through an interaction called rolling or tethering with endothelial cells activated likewise. Thereafter, the leukocytes transmigrate through endothelium to infiltrate into the inflammatory sites (Springer, T A., Annu. Rev. Physiol., 57, 827–872 (1995)). In adhesion of leukocytes to the vascular endothelial cells in this process, various cell adhesion molecules such as an immunoglobulin superfamily (ICAM-1, VCAM-1 and the like), a selectin family (E-selectin and the like), an integrin family (LFA-1, VLA-4 and the like) and CD44, which are induced on the surfaces of the cells by stimulation by cytokines or the like, play important roles ("Rinsho Meneki (Clinical Immune)", 30, Supple. 18 (1998)) and a relationship between the disorder state and aberrant expression of the cell adhesion molecules is noted.

Accordingly, an agent capable of inhibiting cell adhesion can be useful as an agent for preventing and treating allergic diseases such as bronchial asthma, dermatitis, rhinitis and conjunctivitis; autoimmune diseases such as rheumatoid arthritis, nephritis, inflammatory bowel diseases, diabetes and arteriosclerosis; and chronic inflammatory diseases. In fact, it has been reported that antibodies against adhesion molecules on leukocytes such as LFA-1, Mac-1 and VLA-4 on antibodies against ICAM-1, VCAM-1, P-selectin, E-selectin and the like on vascular endothelial cells, which become ligands thereof, inhibit infiltration of leukocytes into inflammatory sites in animal models. For example, neutralizing antibodies against VCAM-1 and VLA-4, which is a counter receptor thereof, can delay development of diabetes in an NOD mouse model which spontaneously causes the diabetes (Michie, S A. et al., Curr. Top. Microbiol. Immunol., 231, 65–83 (1998)). It has also been reported that an antibody against VLA-4 or ICAM-1 and its counter receptor, LFA-1, inhibits infiltration of eosinophils in a guinea pig and mouse allergic conjunctivitis model (Ebihara et al., Current Eye Res., 19, 20–25 (1999); Whitcup, S M et al., Clin. Immunol., 93, 107–113 (1999)), and a monoclonal antibody against VCAM-1 inhibits infiltration of leukocytes in a mouse DSS-induced colitis model to attenuate colitis (Soriano, A. et al., Lab. Invest., 80, 1541–1551 (2000)). Further, an anti-VLA-4 antibody and an anti-CD44 antibody reduce the incidence of disease symptoms in a mouse collagen arthritis model (Zeidler, A. et al., Autoimmunity, 21, 245–252 (1995)). Even in cell adhesion molecule deficient-mice, inhibition of infiltration of leukocytes into inflammatory tissues is observed likewise in inflammatory models (Bendjelloul, F. et al., Clin. Exp. Immunol., 119, 57–63 (2000); Wolyniec, W W. et al., Am. J. Respir. Cell Mol. Biol., 18, 777–785 (1998); Bullard, D C. et al., J. Immunol., 157, 3153–3158 (1996)).

However, it is difficult to develop antibody-based drugs because they are polypeptides and so oral administration is a problem. Moreover, the possible side effects due to antigenicity and allergic reactions are problems.

On the other hand, there have been various investigations of low-molecular weight compounds having an inhibitory effect on cell adhesion with a view toward permitting oral administration. These compounds include benzothiophene derivatives (Boschelli, D H. et al., J. Med. Chem., 38, 4597–4614 (1995)), naphthalene derivatives (Japanese Patent Application Laid-Open No. 10-147568), hydroxybenzoic acid derivatives (Japanese Patent Application Laid-Open No. 10-182550), lignans (Japanese Patent Application Laid-Open No. 10-67656), 2-substituted benzothiazole derivatives (Japanese Patent Application Laid-Open No. 2000-086641 through PCT route), condensed pyrazine compounds (Japanese Patent Application Laid-Open No. 2000-319277 through PCT route), 2,6-dialkyl-4-silylphenol (Japanese Patent Application Laid-Open Re-Publication No. 2000-509070 through PCT route) and the like. However, the goal has not often been sufficiently achieved under the circumstances. Cyclic diamine compounds described in Japanese Patent Application Laid-Open Nos. 9-143075 and 11-92382 do not exhibit a sufficient inhibitory effect on cell adhesion, and so there is a demand for further improvement in activity.

SUMMARY OF THE INVENTION

An object of the present invention is to provide a substance having inhibitory effects on both cell adhesion and cell infiltration, plus excellent anti-asthmatic effects, anti-allergic effects, anti-rheumatic effects, anti-arteriosclerotic effects and anti-inflammatory effects.

With the foregoing circumstances in mind, the present inventors carried out an extensive investigation to find a substance which inhibits cell adhesion and cell infiltration. As a result, we found that compounds represented by the general formula (1), have excellent cell adhesion-inhibiting effects and cell infiltration-inhibiting effects and are useful as anti-allergic agents, anti-asthmatic agents, anti-rheumatic agents, anti-arteriosclerotic agents or anti-inflammatory agents.

The present invention provides a cyclic diamine compound represented by the following general formula (1):

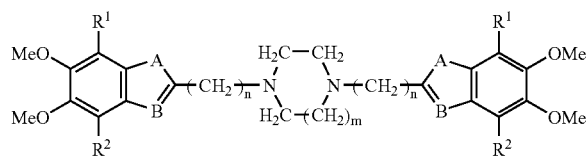

wherein $R^1$ and $R^2$ are individually a hydrogen atom or a methoxy group, provided $R^1$ is a methoxy group when $R^2$ is a hydrogen atom, or $R^1$ is a hydrogen atom when $R^2$ is a methoxy group; A is an oxygen atom, a sulfur atom, CH=CH, CH=N or $NR^3$, in which $R^3$ is a hydrogen atom, or a lower alkyl, hydroxy lower alkyl, lower alkoxy lower alkyl, aryl or aryl lower alkyl group; B is a nitrogen atom, CH or $CR^4$, in which $R^4$ is a hydrogen atom, or a lower alkyl, hydroxy lower alkyl, lower alkoxy lower alkyl, aryl or aryl lower alkyl group; m is 1 or 2; and n is a number of 1 to 5, an acid-addition salt thereof, or a hydrate thereof.

According to the present invention, there is also provided a medicine comprising the above cyclic diamine compound, a salt thereof, or a hydrate thereof as an active ingredient.

According to the present invention, there is further provided a medicinal composition comprising the above cyclic diamine compound, the salt thereof, or the hydrate thereof and a pharmaceutically acceptable carrier.

According to the present invention, there is still further provided a method for treating a disease caused by cell adhesion and/or cell infiltration, which comprises administering an effective amount of the above cyclic diamine compound, a salt thereof, or a hydrate thereof to a patient who requires such treatment.

DETAILED DESCRIPTION OF THE PREFERRED EMBODIMENTS

The lower alkyl groups represented by $R^3$ and $R^4$ in general formula (1) include $C_1$–$C_6$-alkyl groups, for example, methyl, ethyl, n-propyl, isopropyl, n-butyl, isobutyl, tert-butyl, n-pentyl and n-hexyl groups, with methyl, ethyl, n-propyl and isopropyl groups being particularly preferred.

The hydroxy lower alkyl groups include hydroxy-$C_2$–$C_6$-alkyl groups, for example, 2-hydroxyethyl, 2-hydroxy-1-methylethyl, 2-hydroxy-1,1-dimethylethyl, 3-hydroxypropyl, 3-hydroxy-2-methylpropyl, 4-hydroxybutyl, 5-hydroxypentyl and 6-hydroxyhexyl groups, with 2-hydroxyethyl, 2-hydroxy-1-methylethyl, 2-hydroxy-1,1-dimethylethyl and 3-hydroxy-propyl groups being particularly preferred.

The lower alkoxy lower alkyl groups include $C_1$–$C_6$-alkoxy-$C_1$–$C_6$-alkyl groups, for example, 2-methoxyethyl, 2-methoxy-1-methylethyl, 2-methoxy-1,1-dimethylethyl, 3-methoxypropyl, 3-methoxy-2-methylpropyl, 4-methoxybutyl, 5-methoxypentyl, 6-methoxyhexyl, 2-ethoxyethyl, 2-ethoxy-1-methylethyl, 2-ethoxy-1,1-dimethylethyl, 3-ethoxypropyl, 3-ethoxy-2-methylpropyl, 4-ethoxybutyl, 5-ethoxypentyl, 6-ethoxyhexyl, 2-propoxyethyl, 2-propoxy-1-methylethyl, 2-propoxy-1,1-dimethylethyl, 3-propoxypropyl, 3-propoxy-2-methylpropyl, 4-propoxybutyl, 5-propoxypentyl, 6-methoxyhexyl, 2-butoxyethyl, 2-butoxy-1-methylethyl, 2-butoxy-1,1-dimethylethyl, 3-butoxypropyl, 3-butoxy-2-methylpropyl, 4-butoxybutyl, 5-butoxypentyl, 6-butoxyhexyl, 2-pentyloxyethyl, 2-pentyloxy-1-methylethyl, 2-pentyloxy-1,1-dimethylethyl, 3-pentyloxypropyl, 3-pentyloxy-2-methylpropyl, 4-pentyloxybutyl, 5-pentyloxypentyl, 6-pentyloxyhexyl, 2-hexyloxyethyl, 2-hexyloxy-1-methylethyl, 2-hexyloxy-1,1-dimethylethyl, 3-hexyloxypropyl, 3-hexyloxy-2-methylpropyl, 4-hexyloxybutyl, 5-hexyloxypentyl and 6-hexyloxyhexyl groups, with 2-methoxyethyl, 2-methoxy-1-methylethyl, 2-methoxy-1,1-dimethylethyl, 3-methoxypropyl, 2-ethoxyethyl, 2-ethoxy-1-methylethyl, 2-ethoxy-1,1-dimethylethyl, 3-ethoxypropyl, 2-propoxyethyl, 2-propoxy-1-methylethyl, 2-propoxy-1,1-dimethylethyl and 3-propoxypropyl groups being particularly preferred.

The aryl groups include $C_6$–$C_{10}$-aryl groups, for example, a phenyl group. The aryl lower alkyl groups include $C_1$–$C_{10}$-aryl-$C_1$–$C_6$-alkyl groups, for example, phenethyl and benzyl groups.

For $R^3$ and $R^4$, particularly preferred are hydrogen atoms, $C_1$–$C_6$-alkyl groups or phenyl groups, with hydrogen atoms, methyl groups or phenyl groups being further preferred.

In the ring system represented by

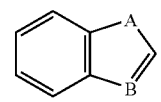

in general formula (1), a skeleton selected from naphthalene, quinoline, quinazoline, benzimidazole, benzothiazole, benzoxazole, indole, benzothiophene and benzofuran is preferred.

The variable n is preferably a number from 1 to 5, more preferably 1 to 4, with a number from 1 to 3 being particularly preferred.

No particular limitation is imposed on the acid-addition salts of the compounds (1) according to the invention as long as they are pharmaceutically acceptable salts. Examples include the acid-addition salts of mineral acids, such as hydrochlorides, hydrobromides, hydriodides, sulfates and phosphates; and acid-addition salts of organic acids, such as benzoates, methanesulfonates, ethanesulfonates, benzenesulfonates, p-toluenesulfonates, oxalates, maleates, fumarates, tartrates, citrates and acetates.

The compounds of formula (1) may be present in the form of solvates typified by hydrates, and the solvates are embraced in the present invention.

The compounds of formula (1) can be prepared in accordance with the following process A or B:

Process A

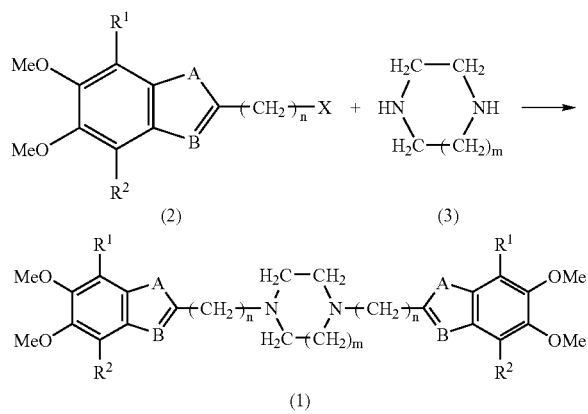

wherein X is a halogen atom, or an alkylsulfonyloxy or arylsulfonyloxy group, and $R^1$, $R^2$, A, B, m and n have the same meanings as defined above.

More specifically, compounds of formula (1) are obtained by condensing a compound (2) with a cyclic diamine (3). As the halogen atom represented by X in the general formula (2), a chlorine or bromine atom is preferred. As the alkylsulfonyloxy group, the methanesulfonyloxy group is preferred. As the arylsulfonyloxy group, the p-toluenesulfonyloxy group is preferred.

The condensation reaction of compound (2) with cyclic diamine (3) is conducted by, for example, stirring the reaction mixture at 0° C. to 100° C., preferably room temperature for 1 hour to several days in the presence of a base such as potassium carbonate in a solvent such as N,N-dimethylformamide (DMF), dimethyl sulfoxide (DMSO) or acetonitrile.

The compound (2) used in this reaction can be prepared in accordance with, for example, the following reaction formula:

wherein $R^5$ is a hydrogen atom or a lower alkyl group, and $R^1$, $R^2$, A, B, n and X have the same meanings as defined above.

More specifically, a carboxylic acid or ester thereof (4), or an aldehyde (5) thereof is reduced with a reducing agent such as lithium aluminum hydride to form an alcohol (6). The alcohol is reacted with a halogenating agent such as thionyl chloride, or sulfonilating agent such as methanesulfonyl chloride, p-toluenesulfonyl chloride or the like, thereby obtaining the compound (2). The alcohol (6) may also be obtained by a hydroboration followed by oxidation of a terminal olefin.

The compound (2) having a quinazoline skeleton can be prepared in accordance with the following reaction formula:

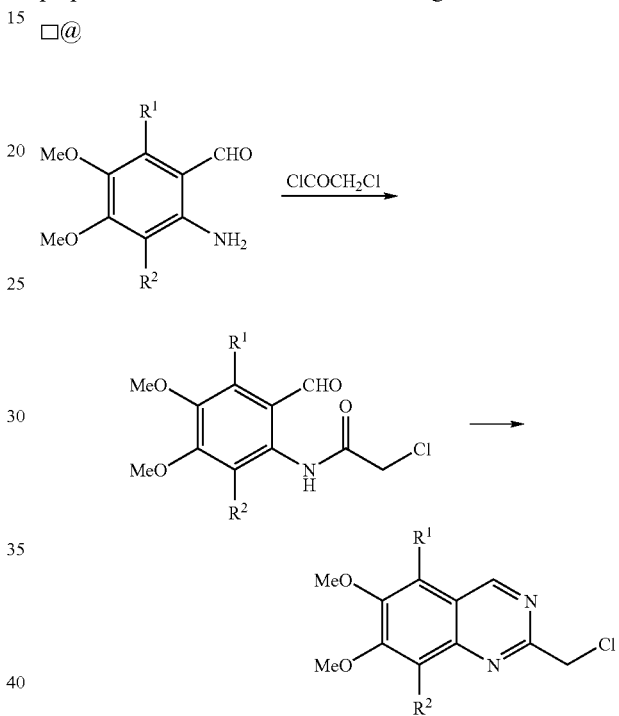

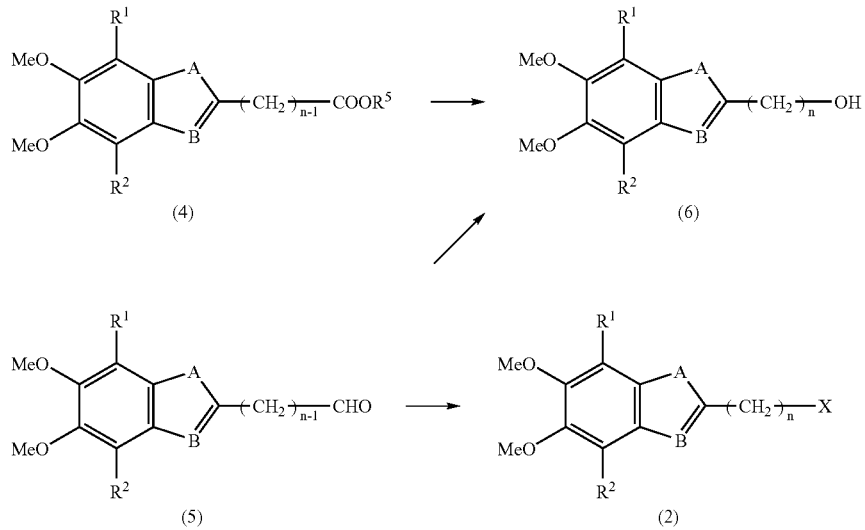

Process B

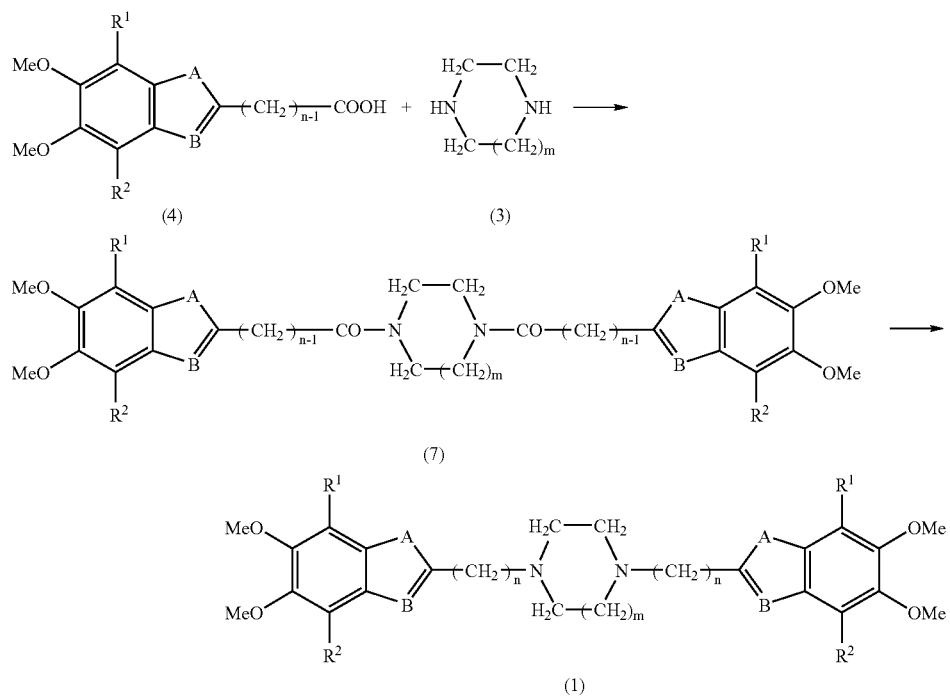

wherein $R^1$, $R^2$, A, B, m and n have the same meanings as defined above.

More specifically, compound (1) according to the present invention is obtained by condensing the carboxylic acid (4) with the cyclic diamine (3) and reducing the resultant amide (7).

The condensation reaction of the carboxylic acid (4) with the cyclic diamine (3) is conducted by, for example, reacting the reaction mixture at 0° C. to a reflux temperature, preferably room temperature for 1 hour to several days, preferably overnight using N,N-dimethylaminopyridine as a catalyst and a dehydration-condensing agent such as dicyclohexylcarbodiimide or 1-ethyl-3-(3-dimethylaminopropyl)carbodiimide hydrochloride (water-soluble carbodiimide hydrochloride) in a solvent such as toluene, benzene, dichloromethane, chloroform, tetrahydrofuran (THF), dioxane or acetonitrile. The reduction reaction of the amide (7) is conducted by, for example, reacting the amide (7) at 0° C. to a reflux temperature, preferably room temperature for 1 hour to several days, preferably 6 hours using a reducing agent such as lithium aluminum hydride in THF or diethyl ether.

The compounds (1) according to the present invention are obtained by any of the above-described processes and may further be purified by using an ordinary purification means such as recrystallization or column chromatography as needed. As needed, the compounds may also be converted into the desired salts or solvates in a method known per se in the art. When the compounds (1) have an asymmetric carbon atom, the present invention include any configurational isomers.

The compounds (1) according to the present invention, or salts or solvates thereof thus obtained have an excellent inhibitory effect on cell adhesion as demonstrated in the examples, which will be described subsequently, and are useful as medicines for treatment and prevention of diseases of animals including humans, caused by cell adhesion or cell infiltration, for example, asthma, allergy, rheumatism, arteriosclerosis, inflammation, etc.

The medicine according to the present invention comprises a compound (1), a salt thereof, or a solvate thereof as an active ingredient. The form of administration may be suitably selected as necessary for the therapeutic application intended without any particular limitation, including oral preparations, injections, suppositories, ointments, inhalants, eye drops, nose drops and plasters. A composition suitable for use in these administration forms can be prepared by blending a pharmaceutically acceptable carrier in accordance with the conventional preparation method publicly known by those skilled in the art.

When an oral solid preparation is formulated, an excipient, and optionally, a binder, disintegrator, lubricant, colorant, a taste corrigent, a smell corrigent and the like are added to compound (1) and the resulting composition can be formulated into tablets, coated tablets, granules, powders, capsules, etc. in accordance with methods known in the art.

As such additives described above, any additives may be used which are generally used in the pharmaceutical field. Examples include excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dry starch, sodium alginate, agar powder, sodium hydrogencarbonate, calcium carbonate, sodium lauryl sulfate, monoglyceryl stearate and lactose; lubricants such as purified talc, stearic acid salts, borax and polyethylene glycol; and taste corrigents such as sucrose, orange peel, citric acid and tartaric acid.

When an oral liquid preparation is formulated, a taste corrigent, buffer, stabilizer, smell corrigent and/or the like are added to compound (1) and the resulting composition can be formulated into internal liquid preparations, syrup preparations, elixirs, etc. in accordance with methods known in the art. In this case, vanillin as the taste corrigent, may be used. As the buffer, sodium citrate may be mentioned. As examples of the stabilizer, tragacanth, gum arabic and gelatin may be mentioned.

When an injection is formulated, a pH adjustor, buffer, stabilizer, isotonicity agent, local anesthetic and the like may be added to compound (1) according to the present invention, and the resultant composition can be formulated into subcutaneous, intramuscular and intravenous injections in accordance with methods known in the art. Examples of the pH adjustor and buffer in this case include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the isotonicity agent include sodium chloride and glucose.

When a suppository is formulated, a carrier preparation known in the art, for example, polyethylene glycol, lanoline, cacao butter, fatty acid triglyceride or the like, and optionally, a surfactant such as Tween (trade mark) and the like are added to the compound (1), and the resultant composition can be formulated into suppositories in accordance with methods known in the art.

When an ointment is formulated, a base material, stabilizer, wetting agent, preservative and the like, which are generally used, are blended with compound (1) as needed, and the resulting blend is mixed and formulated into ointments in accordance with known method known methods. Examples of the base material include liquid paraffin, white vaseline, bleached beeswax, octyldodecyl alcohol and paraffin. Examples of the preservative include methyl p-hydroxybenzoate, ethyl p-hydroxybenzoate and propyl p-hydroxybenzoate.

Besides the above preparations, inhalants, eye drops and nose drops may also be formulated in accordance with known methods.

The dose of the medicine according to the present invention varies according to the age, weight and condition of the patient to be treated, the administration method, the number of times of administration, and the like. It is however preferred that the medicine is generally orally or parenterally administered at once or in several portions in a dose of 1 to 1,000 mg per day in terms of compound (1), for an adult.

The present invention will hereinafter be described in more detail by Examples. However, the present invention is not limited to these examples.

PREPARATION EXAMPLE 1

Synthesis of
5,6,7-trimethoxynaphthalene-2-carbonitrile 2.0 M Lithium diisopropylamide (2.55 mL) was added dropwise to dry THF (5 mL) at −78° C. under an argon atmosphere, and the mixture was stirred for 30 minutes. A solution of 3-cyanopropionaldehyde dimethylacetal (672 mg) in dry THF (5 mL) was then added dropwise to the mixture, and the resulting mixture was stirred at −78° C. for 1 hour. A solution of 3,4,5-trimethoxybenzaldehyde (1.0 g) in dry THF (5 mL) was then added dropwise to the reaction mixture. After stirring at room temperature for 1 hour, a saturated aqueous solution of ammonium chloride was added to the reaction mixture to conduct extraction with ethyl acetate. The resultant organic layer was washed with saturated brine, dried over anhydrous magnesium sulfate and then concentrated under reduced pressure. The resultant residue was dissolved in methanol (6 mL), sulfuric acid (1 mL) was slowly added to the solution, and the mixture was stirred at 100° C. for 1 hour. The reaction mixture was weakly alkalified with a 4 M aqueous solution of potassium hydroxide at 0° C. to conduct extraction with chloroform. The resultant organic layer was washed with water and saturated brine, dried over anhydrous magnesium sulfate and then concentrated under reduced pressure. The residue was purified by column chromatography on silica gel (ethyl acetate:hexane=1:3 to 1:1) to obtain the title compound.

Yield: 847 mg (68.3%).

PREPARATION EXAMPLE 2

Synthesis of
5,6,7-trimethoxynaphthalene-2-carboxylic acid 5,6,7-Trimethoxynaphthalene-2-carbonitrile (5.8 g) obtained above was dissolved in ethanol (40 mL), a solution of potassium hydroxide (11.2 g) in water (10 mL) was added to the solution, and the mixture was stirred for 1 hour under reflux. After cooling, the solvent was distilled off, the residue was dissolved in water, and the solution was washed twice with ether. The resultant water layer was then neutralized with diluted hydrochloric acid. The thus-neutralized water layer was then extracted with ethyl acetate, the resultant extract was washed with saturated brine and water and dried over anhydrous magnesium sulfate, and the solvent was then distilled off to obtain the title compound.

Yield: 5.2 g (85%).

$^1$H-NMR (400 MHz, CDCl$_3$) δ: 4.00(s, 3H), 4.02(s, 3H), 4.06(s, 3H), 7.08(s, 1H), 8.00(dd, 1H, J=8.8 Hz, 1.7 Hz), 8.12(d, 1H, J=8.8 Hz), 8.55(d, 1H, J=1.5 Hz).

PREPARATION EXAMPLE 3

Synthesis of
2-hydroxymethyl-5,6,7-trimethoxynaphthalene

Lithium aluminum hydride (579 mg) was added to dry THF (40 mL) under an argon atmosphere and ice cooling, a solution of 5,6,7-trimethoxynaphthalene-2-carboxylic acid (4.0 g) in dry THF (40 mL) was then added dropwise thereto, and the mixture was stirred at room temperature for 4 hours. Ether (150 mL) was added to the reaction mixture, sodium sulfate decahydrate was added thereto, and the resultant mixture was stirred for 15 minutes. The reaction mixture was filtered, the filtrate was concentrated, and the residue was purified by column chromatography on silica gel (ethyl acetate:hexane=1:2) to obtain the title compound.

Yield: 3.8 g (theoretical amount).

$^1$H-NMR (400 MHz, CDCl$_3$) δ: 3.97(s, 6H), 4.04(s, 3H), 4.82(d, 2H, J=5.6 Hz), 6.93(s, 1H), 7.35(dd, 1H, J=8.6 Hz, 1.7 Hz), 7.66(s, 1H), 8.03(d, 1H, J=8.6 Hz).

PREPARATION EXAMPLE 4

Synthesis of 2-chloromethyl-5,6,7-trimethoxynaphthalene

2-Hydroxymethyl-5,6,7-trimethoxynaphthalene (781 mg) was dissolved in chloroform (6 mL), and thionyl chloride (561 mL) was added dropwise to the solution. After stirring at room temperature for 5 hours, the reaction mixture was poured into ice water, and sodium hydrogencarbonate was added to adjust the pH of the reaction mixture to 8 to conduct extraction with ethyl acetate. The resultant organic layer was washed with saturated brine, dried over anhydrous magnesium sulfate and then concentrated under reduced pressure to obtain the title compound.

Yield: 608 mg (73%).

$^1$H-NMR (400 MHz, CDCl$_3$) δ: 3.96(s, 3H), 3.97(s, 3H), 4.03(s, 3H), 4.71(s, 2H), 6.29(s, 1H), 7.36(dd, 1H, J=8.6 Hz, 1.5 Hz).

EXAMPLE 1

Synthesis of N,N'-bis[(5,6,7-trimethoxynaphthalen-2-yl)methyl]piperazine

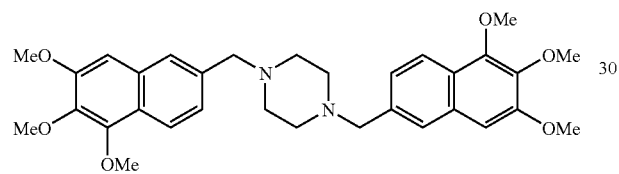

2-Chloromethyl-5,6,7-trimethoxynaphthalene (418 mg) and piperazine (63 mg) were dissolved in DMF (10 mL), potassium carbonate (207 mL) was added to the solution, and the mixture was stirred at room temperature for 5 hours. After concentrating the reaction mixture under reduced pressure, chloroform was added to the residue, and the mixture was washed with water and saturated brine, dried over anhydrous magnesium sulfate and then concentrated under reduced pressure. The residue was purified by column chromatography on silica gel (chloroform:methanol=40:1) to obtain the title compound as a free base.

Yield: 109 mg (27%).

$^1$H-NMR (hydrochloride, 400 MHz, DMSO-d$_6$) δ: 3.35(s, 8H), 3.89(s, 6H), 3.94(s, 6H), 3.99(s, 6H), 4.29(s, 4H), 7.11(s, 2H), 7.56(d, 2H, J=10.2 Hz), 7.95(s, 2H), 7.96(d, 2H, J=10.2 Hz).

m/z (EI): 546 [M$^+$].

EXAMPLE 2

Synthesis of N,N'-bis[(5,6,7-trimethoxynaphthalen-2-yl)methyl]homopiperazine

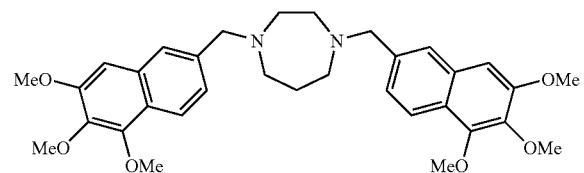

2-Chloromethyl-5,6,7-trimethoxynaphthalene (607 mg) and homopiperazine (108 mg) were reacted in the same manner in Example 1 to obtain the title compound as a free base.

Yield: 314 mg (51%).

$^1$H-NMR (hydrochloride, 400 MHz, DMSO-d$_6$) δ: 2.30 (quint, 2H, J=6.8 Hz), 3.40(t, 4H, J=6.8 Hz), 3.71(s, 4H), 3.89(s, 6H), 3.93(s, 6H), 3.99(s, 6H), 4.42(s, 4H), 7.11(s, 2H), 7.58(dd, 2H, J=8.8 Hz, 1.7 Hz), 7.96(d, 2H, J=8.8 Hz), 7.98(d, 2H, J=1.7 Hz).

m/z (EI): 560 [M$^+$].

PREPARATION EXAMPLE 5

Synthesis of 6,7,8-trimethoxynaphthalene-2-carbonitrile 2,3,4-Trimethoxybenzaldehyde (9.8 g) and 3-cyanopropionaldehyde dimethylacetal (6.35 mL) were treated under the same conditions as in Preparation Example 1 to obtain the title compound.

Yield: 5.94 g (49%).

PREPARATION EXAMPLE 6

Synthesis of 6,7,8-trimethoxynaphthalene-2-carboxylic acid 6,7,8-Trimethoxynaphthalene-2-carbonitrile (2.34 g) was treated in the same manner as in Preparation Example 2 to obtain the title compound.

Yield: 2.3 g (91%).

$^1$H-NMR (400 MHz, CDCl$_3$) δ: 3.99(s, 3H), 4.02(s, 3H), 4.12(s, 3H), 6.99(s, 1H), 7.74(d, 1H, J=8.4 Hz), 8.04(dd, 1H, J=8.4 Hz, 1.8 Hz), 8.91(d, 1H, J=1.8 Hz).

PREPARATION EXAMPLE 7

Synthesis of 2-hydroxymethyl-6,7,8-trimethoxynaphthalene 6,7,8-Trimethoxynaphthalene-2-carboxylic acid (5.7 g) was treated in the same manner as in Preparation Example 3 to obtain the title compound.

Yield: 5.2 g (96%).

$^1$H-NMR (400 MHz, CDCl$_3$) δ: 3.97(s, 3H), 3.97(s, 3H), 4.06(s, 3H), 4.83(d, 2H, J=5.9 Hz) 6.95(s, 1H), 7.41(dd, 1H, J=8.4 Hz, 1.8 Hz), 7.69(dd, 1H, J=8.4 Hz, 1.8 Hz), 8.01(s, 1H).

PREPARATION EXAMPLE 8

Synthesis of 2-chloromethyl-6,7,8-trimethoxynaphthalene

2-Hydroxymethyl-6,7,8-trimethoxynaphthalene (656 mg) was treated in the same manner as in Preparation Example 4 to obtain the title compound.

Yield: 508 mg (76%).

$^1$H-NMR (400 MHz, CDCl$_3$) δ: 3.97(s, 6H), 4.06(s, 3H), 4.88(s, 2H), 6.95(s, 1H), 7.41(dd, 1H, J=8.4 Hz, 1.8 Hz), 7.69(dd, 1H, J=8.4 Hz, 1.8 Hz).

EXAMPLE 3

Synthesis of N,N'-bis[(6,7,8-trimethoxynaphthalen-2-yl)methyl]piperazine

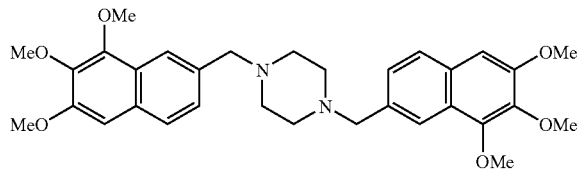

2-Chloromethyl-6,7,8-trimethoxynaphthalene (226 mg) and piperazine (37 mg) were reacted in the same manner in Example 1 to obtain the title compound as a free base.

Yield: 214 mg (92%).

$^1$H-NMR (400 MHz, CDCl$_3$) δ: 2.53(br, 8H), 3.49(s, 4H), 3.96(s, 12H), 4.05(s, 6H), 6.93(s, 2H), 7.41(dd, 2H, J=8.2 Hz, 1.6 Hz), 7.63(d, 2H, J=8.2 Hz), 7.91(br, 2H).

m/z (EI): 546 [M$^+$].

EXAMPLE 4

Synthesis of N,N'-bis[(6,7,8-trimethoxynaphthalen-2-yl)methyl]homopiperazine

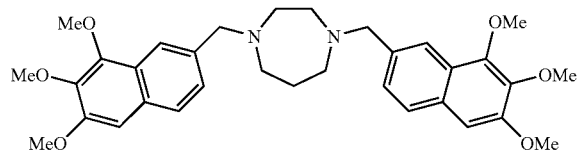

2-Chloromethyl-6,7,8-trimethoxynaphthalene (222 mg) and homopiperazine (42 mg) were reacted in the same manner in Example 1 to obtain the title compound as a free base.

Yield: 168 mg (72%).

$^1$H-NMR (400 MHz, CDCl$_3$) δ: 1.86(br, 2H), 2.77(t, 4H, J=5.9 Hz), 2.82(t, 4H, J=5.9 Hz), 3.82(s, 4H), 3.96(s, 12H), 4.04(s, 6H), 6.93(s, 2H), 7.47(dd, 2H, J=8.4 Hz, 1.5 Hz), 7.64(d, 2H, J=8.3 Hz), 7.91(br, 2H).

m/z (EI): 560 [M$^+$].

PREPARATION EXAMPLE 9

Synthesis of 5,6,7-trimethoxynaphthalene-2-carboaldehyde

2-Hydroxymethyl-5,6,7-trimethoxynaphthalene (3.78 g) was dissolved in dichloromethane (100 mL), pyridium dichromate (8.61 g) was added to the solution, and the mixture was stirred at room temperature for 4 hours. The reaction mixture was filtered, and insoluble matter was fully washed with chloroform. After the washings were combined with the filtrate and concentrated under reduced pressure, the residue was dissolved in ethyl acetate, and the solution was successively washed with 2 M hydrochloric acid, water and saturated brine, dried over anhydrous magnesium sulfate and then concentrated under reduced pressure. The residue was purified by column chromatography on silica gel (ethyl acetate:hexane=1:3 to 1:1) and further recrystallized from ethyl acetate-hexane to obtain the title compound.

Yield: 3.24 g (86%).

$^1$H-NMR (400 MHz, CDCl$_3$) δ: 4.01(s, 3H), 4.02(s, 3H), 4.05(s, 3H), 7.10(s, 1H), 7.82(dd, 1H, J=8.7 Hz, 1.6 Hz), 8.15(d, 1H, J=8.7 Hz), 8.19(d, 1H, J=1.5 Hz), 10.11(s, 1H).

PREPARATION EXAMPLE 10

Synthesis of 5,6,7-trimethoxy-2-vinylnaphthalene

Methyltriphenylphosphonium bromide (2.8 g) was suspended in dry THF (10 mL) under an argon atmosphere, and a 1.7 M hexane solution (3.3 mL) of tert-butyllithium was added to the suspension at −20° C. After stirring the mixture at room temperature for 1 hour, the reaction mixture was cooled again to −20° C., a solution of 5,6,7-trimethoxynaphthalene-2-carboaldehyde (1.26 g) in dry THF (30 mL) was added dropwise thereto, and the mixture was stirred overnight at room temperature. The solvent was distilled off, and water was added to the residue to conduct extraction with ethyl acetate. The resultant organic layer was washed with water and saturated brine, dried over anhydrous magnesium sulfate and then concentrated under reduced pressure. The residue was purified by column chromatography on silica gel (ethyl acetate:hexane=1:8) to obtain the title compound.

Yield: 1.15 g (93%).

$^1$H-NMR (400 MHz, CDCl$_3$) δ: 3.93(s, 3H), 3.98(s, 3H), 4.04(s, 3H), 5.31(d, 1H, J=10.9 Hz), 5.85(d, 1H, J=17.6 Hz), 6.83(dd, 1H, J=17.5, 10.7 Hz), 6.90(s, 1H), 7.51(dd, 1H, J=8.7, 1.7 Hz), 7.59(s, 1H), 8.01(d, 1H, J=8.6 Hz).

PREPARATION EXAMPLE 11

Synthesis of 2-(2-hydroxyethyl)-5,6,7-trimethoxynaphthalene 5,6,7-Trimethoxy-2-vinylnaphthalene (1.215 g) was dissolved in dry THF (10 mL) under an argon atmosphere, a 1 M THF solution (4.7 mL) of borane was added dropwise to the solution at 0° C., and the mixture was stirred at room temperature for 2 hours. Water (4 mL) was added to the reaction mixture at 0° C., and a 4 M aqueous solution (1.2 mL) of sodium hydroxide was then added. 31% Aqueous hydrogen peroxide (0.5 mL) was added to the reaction mixture at 0° C., and the mixture was stirred at 50° C. for 50 minutes. The solvent was distilled off, and water was added to the residue to conduct extraction with ethyl acetate. The resultant organic layer was washed with water and saturated brine, dried over anhydrous magnesium sulfate and then concentrated under reduced pressure. The residue was purified by column chromatography on silica gel (ethyl acetate:hexane=1:8) to obtain the title compound.

Yield: 1.03 g (83.5%).

$^1$H-NMR (400 MHz, CDCl$_3$) δ: 2.02(br, 1H), 2.95(d, 1H, J=6.6 Hz), 3.87(t, 2H, J=6.6 Hz), 3.93(s, 3H), 3.95(s, 3H), 4.02(s, 3H), 6.88(s, 1H), 7.20(dd, 1H, J=8.5 Hz, 1.7 Hz), 7.50(s, 1H), 7.97(d, 1H, J=8.6 Hz).

PREPARATION EXAMPLE 12

Synthesis of 2-(2-methanesulfonyloxyethyl)-5,6,7-trimethoxynaphthalene 2-(2-Hydroxyethyl)-5,6,7-trimethoxynaphthalene (1.26 g) was dissolved in pyridine (5 mL), methanesulfonyl chloride (715 mg) was added at 0° C. to the solution, and the mixture was stirred at room temperature for 2 hours. The reaction mixture was acidified with hydrochloric acid and extracted with ethyl acetate. The resultant extract was washed with water and saturated brine. The solvent was distilled off under reduced pressure, and the residue was purified by column chromatography on silica gel (ethyl acetate:hexane=1:5) to obtain the title compound.

Yield: 1.55 g (95%).

$^1$H-NMR (400 MHz, CDCl$_3$) δ: 2.84(s, 3H), 3.18(t, 2H, J=6.9 Hz), 3.96(s, 3H), 3.97(s, 3H), 4.04(s, 3H), 4.49(t, 2H, J=6.9 Hz), 6.90(s, 1H), 7.22(dd, 1H, J=9.4 Hz, 1.2 Hz), 7.54(s, 1H), 8.00(d, 1H, J=8.6 Hz).

EXAMPLE 5

Synthesis of N,N'-bis[2-(5,6,7-trimethoxynaphthalen-2-yl)ethyl]piperazine

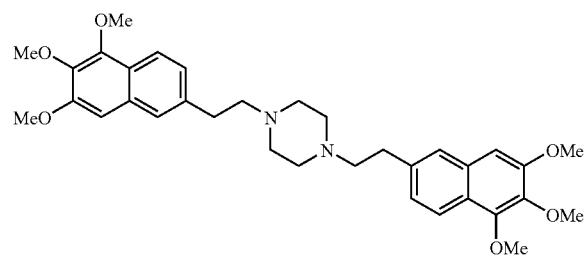

2-(2-Methanesulfonyloxyethyl)-5,6,7-trimethoxynaphthalene (374 mg) and piperazine (43 mg) were reacted in the same manner in Example 1 to obtain the title compound as a free base.

Yield: 65 mg (23%).

$^1$H-NMR (400 MHz, CDCl$_3$) δ: 2.64–2.74(m, 12H), 2.89–3.00(m, 4H), 3.96(s, 6H), 3.96(s, 6H), 4.03(s, 6H), 6.89(s, 2H), 7.23(dd, 2H, J=8.6 Hz, 1.6 Hz), 7.50(s, 2H), 7.96(d, 2H, J=8.6 Hz).

m/z (EI): 574 [M$^+$].

EXAMPLE 6

Synthesis of N,N'-bis[2-(5,6,7-trimethoxynaphthalen-2-yl)ethyl]homopiperazine

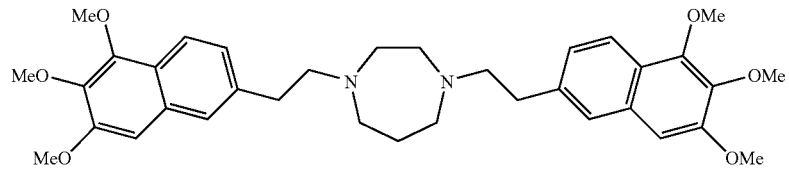

2-(2-Methanesulfonyloxyethyl)-5,6,7-trimethoxynaphthalene (225 mg) and homopiperazine (52 mg) were reacted in the same manner in Example 1 to obtain the title compound as a free base.

Yield: 58 mg (33%).

$^1$H-NMR (400 MHz, CDCl$_3$) δ: 1.79–1.82(m, 2H), 2.75–2.85(m, 16H), 3.84(s, 6H), 3.85(s, 6H), 3.93(s, 6H), 6.79(s, 2H), 7.11(dd, 2H, J=8.6 Hz, 1.5 Hz), 7.40(s, 2H), 7.86(d, 2H, J=8.6 Hz).

m/z (EI): 588 [M$^+$].

PREPARATION EXAMPLE 13

Synthesis of 6,7,8-trimethoxynaphthalene-2-carboaldehyde

2-Hydroxymethyl-6,7,8-trimethoxynaphthalene (4.41 g) was treated in the same manner as in Preparation Example 9 to obtain the title compound.

Yield: 3.33 g (77%).

$^1$H-NMR (400 MHz, CDCl$_3$) δ: 3.99(s, 3H), 4.02(s, 3H), 4.13(s, 3H), 6.99(s, 1H), 7.75(d, 1H, J=8.8 Hz), 7.87(dd, 1H, J=8.8 Hz, 1.8 Hz), 8.55(d, 1H, J=1.8 Hz), 10.11(s, 1H).

PREPARATION EXAMPLE 14

Synthesis of 6,7,8-trimethoxy-2-vinylnaphthalene 6,7,8-Trimethoxynaphthalene-2-carboaldehyde (1.23 g) was treated in the same manner as in Preparation Example 10 to obtain the title compound.

Yield: 985 mg (80%).

$^1$H-NMR (400 MHz, CDCl$_3$) δ: 3.97(s, 6H), 4.06(s, 3H), 5.28(d, 1H, J=8.9 Hz), 5.83(d, 1H, J=8.9 Hz), 6.82–6.93(m, 1H), 6.93(s, 1H), 7.55(dd, 1H, J=8.4 Hz, 1.8 Hz), 7.64(d, 1H, J=8.4 Hz), 7.95(br, 1H).

PREPARATION EXAMPLE 15

Synthesis of 2-(2-hydroxyethyl)-6,7,8-trimethoxynaphthalene 6,7,8-Trimethoxy-2-vinylnaphthalene (735 mg) was treated in the same manner as in Preparation Example 11 to obtain the title compound.

Yield: 668 mg (85%).

$^1$H-NMR (400 MHz, CDCl$_3$) δ: 3.02(t, 2H, J=6.6 Hz), 3.93(t, 2H, J=6.6 Hz), 3.97(s, 6H), 4.05(s, 3H), 6.93(s, 1H), 7.28(dd, 1H, J=8.3, 1.7 Hz), 7.65(d, 1H, J=8.3 Hz), 7.88(br, 1H).

PREPARATION EXAMPLE 16

Synthesis of 2-(2-methanesulfonyloxyethyl)-6,7,8-trimethoxynaphthalene 2-(2-Hydroxyethyl)-6,7,8-trimethoxynaphthalene (668 mg) was treated in the same manner as in Preparation Example 12 to obtain the title compound.

Yield: 922 mg (theoretical amount).

$^1$H-NMR (400 MHz, CDCl$_3$) δ: 3.21(t, 2H, J=6.8 Hz), 2.97(s, 6H), 4.01(s, 8H), 4.50(t, 2H, J=2.8 Hz), 6.93(s, 1H), 7.27(dd, 1H, J=8.4 Hz, 1.7 Hz), 7.66(d, 1H, J=8.4 Hz), 7.88(br, 1H).

EXAMPLE 7

Synthesis of N,N'-bis[2-(6,7,8-trimethoxynaphthalen-2-yl)ethyl]piperazine

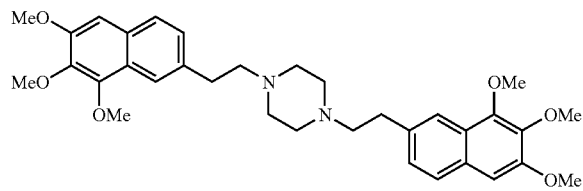

2-(2-Methanesulfonyloxyethyl)-6,7,8-trimethoxynaphthalene (230 mg) and piperazine (29 mg) were reacted in the same manner in Example 1 to obtain the title compound as a free base.

Yield: 13 mg (7%).

$^1$H-NMR (400 MHz, CDCl$_3$) δ: 2.63(br, 8H), 2.70(t, 4H, J=6.8 Hz), 2.95(t, 4H, J=6.8 Hz), 3.57(br, 4H), 3.96(s, 12H), 4.05(s, 6H), 6.92(s, 2H), 7.24(dd, 2H, J=8.3 Hz, 1.7 Hz), 7.62(d, 2H, J=8.3 Hz), 7.84(d, 2H, J=1.7 Hz).

m/z (EI): 574 [M$^+$].

EXAMPLE 8

Synthesis of N,N'-bis[2-(6,7,8-trimethoxynaphthalen-2-yl)ethyl]homopiperazine

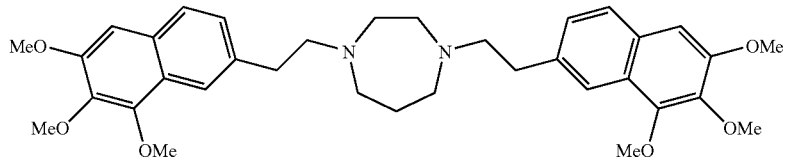

2-(2-Methanesulfonyloxyethyl)-6,7,8-trimethoxynaphthalene (164 mg) and homopiperazine (24 mg) were reacted in the same manner in Example 1 to obtain the title compound as a free base.

Yield: 79 mg (56%).

$^1$H-NMR (400 MHz, CDCl$_3$) δ: 1.90(br, 2H), 2.82–2.98 (m, 16H), 3.96(s, 12H), 4.05(s, 6H), 6.92(s, 2H), 7.24(dd, 2H, J=8.4 Hz, 1.6 Hz), 7.61(d, 2H, J=8.4 Hz), 7.85(s, 2H).

m/z (EI): 588 [M$^+$].

PREPARATION EXAMPLE 17

Synthesis of Ethyl 3-(5,6,7-trimethoxynaphthalen-2-yl)propenoate

55% Sodium hydride (241 mg) was suspended in THF (2.5 mL) at −10° C. under an argon atmosphere, a solution of ethyl diethylphosphonoacetate (1.23 g) in THF (5 mL) was added dropwise to the suspension, and the mixture was stirred for 30 minutes. A solution of 5,6,7-trimethoxynaphthalene-2-carboaldehyde (1.23 g) in THF (10 mL) was then added dropwise, and the mixture was stirred for 30 minutes at −10° C. and 1 hour at room temperature. The reaction mixture was diluted with ethyl acetate, washed with 2 M hydrochloric acid, water and saturated brine, dried over anhydrous magnesium sulfate and then concentrated under reduced pressure. The residue was purified by column chromatography on silica gel (ethyl acetate:hexane=1:2) to obtain the title compound.

Yield: 1.79 g (theoretical amount).

$^1$H-NMR (400 MHz, CDCl$_3$) δ: 1.35(t, 3H, J=7.1 Hz), 3.98(s, 6H), 4.04(s, 3H), 4.24(q, 2H, J=7.1 Hz), 6.53(d, 1H, J=16.1 Hz), 6.96(s, 1H), 7.55(d, 1H, J=8.8 Hz), 7.78(s, 1H), 7.80(d, 1H, J=16.1 Hz), 8.03(d, 1H, J=8.8 Hz).

PREPARATION EXAMPLE 18

Synthesis of Ethyl 3-(5,6,7-Trimethoxynaphthalen-2-yl)propionate

Ethyl 3-(5,6,7-trimethoxynaphthalen-2-yl)propenoate (1.70 g) was dissolved in methanol (20 mL), 10% palladium on carbon (510 mg) was added to the solution, and the mixture was stirred at room temperature for 2.5 hours under a hydrogen atmosphere. The reaction mixture was filtered, and the filtrate was then concentrated to obtain the title compound.

Yield: 1.28 g (81%).

$^1$H-NMR (400 MHz, CDCl$_3$) δ: 1.23(t, 3H, J=7.2 Hz), 2.68(t, 2H, J=7.8 Hz), 3.07(t, 2H, J=7.8 Hz), 3.95(s, 3H), 3.96(s, 3H), 4.03(s, 3H), 4.13(q, 2H, J=7.1 Hz), 6.89(s, 1H), 7.21(dd, 1H, J=8.6 Hz, 1.6 Hz), 7.50(s, 1H), 7.96(d, 1H, J=8.5 Hz).

PREPARATION EXAMPLE 19

Synthesis of 2-(3-hydroxypropyl)-5,6,7-trimethoxynaphthalene

Ethyl 3-(5,6,7-trimethoxynaphthalen-2-yl)propionate (1.28 g) was treated in the same manner as in Preparation Example 3 to obtain the title compound.

Yield: 1.13 g (theoretical amount).

$^1$H-NMR (400 MHz, CDCl$_3$) δ: 1.55(s, 1H), 1.93–2.00(m, 2H), 2.84(t, 2H, J=7.6 Hz), 3.71(dd, 2H, J=6.3 Hz, 2.0 Hz), 3.96(s, 3H), 3.97(s, 3H), 4.04(s, 3H), 6.89(s, 1H), 7.22(dd, 1H, J=8.6 Hz, 1.7 Hz), 7.49(s, 1H), 7.96(d, 1H, J=8.5 Hz).

PREPARATION EXAMPLE 20

Synthesis of 2-(3-methanesulfonyloxypropyl)-5,6,7-trimethoxynaphthalene 2-(3-Hydroxypropyl)-5,6,7-trimethoxynaphthalene (1.26 g) was treated in the same manner as in Preparation Example 12 to obtain the title compound.

Yield: 1.55 g (95%).

$^1$H-NMR (400 MHz, CDCl$_3$) δ: 2.16(quint, 2H, J=7.8 Hz), 2.90(t, 2H, J=7.8 Hz), 3.00(s, 3H), 3.97(s, 6H), 4.05(s, 3H), 4.25(t, 3H, J=7.8 Hz), 6.93(s, 1H), 7.24(dd, 1H, J=8.4 Hz, 1.7 Hz), 7.63(d, 1H, J=8.4 Hz), 7.83(d, 1H, J=1.7 Hz).

EXAMPLE 9

Synthesis of N,N'-bis[3-(5,6,7-trimethoxynaphthalen-2-yl)propyl]piperazine

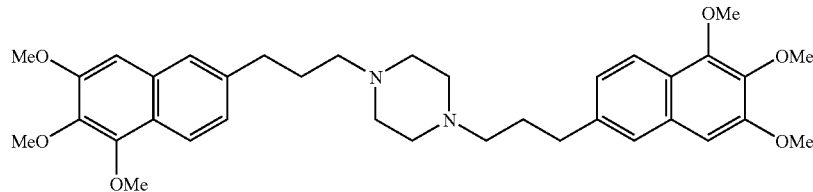

2-(3-Methanesulfonyloxypropyl)-5,6,7-trimethoxynaphthalene (213 mg) and piperazine (26 mg) were reacted in the same manner in Example 1 to obtain the title compound as a free base.

Yield: 152 mg (84%).

$^1$H-NMR (400 MHz, CDCl$_3$) δ: 1.85–1.93(m, 4H), 2.40(t, 4H, J=7.6 Hz), 2.49(br, 8H), 2.75(t, 4H, J=7.6 Hz), 3.95(s, 12H), 4.03(s, 6H), 6.88(s, 2H), 7.20(dd, 2H, J=8.5 Hz, 1.5 Hz), 7.46(s, 2H), 7.94(d, 2H, J=8.5 Hz).

m/z (EI): 602 [M$^+$].

EXAMPLE 10

Synthesis of N,N'-bis[3-(5,6,7-trimethoxynaphthalen-2-yl)propyl]homopiperazine

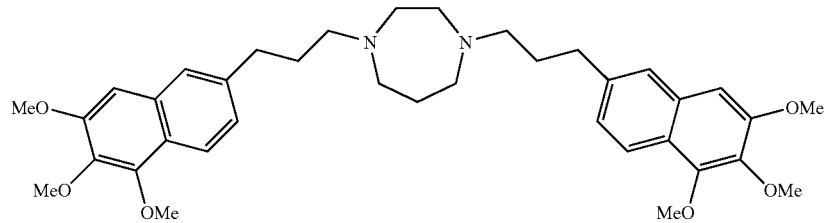

2-(3-Methanesulfonyloxypropyl)-5,6,7-trimethoxynaphthalene (213 mg) and homopiperazine (30 mg) were reacted in the same manner in Example 1 to obtain the title compound as a free base.

Yield: 155 mg (84%).

$^1$H-NMR (400 MHz, CDCl$_3$) δ: 1.78–1.90(m, 6H), 2.53(t, 4H, J=7.4 Hz), 2.69–2.77(m, 12H), 3.95(s, 12H), 4.03(s, 6H), 6.87(s, 2H), 7.20(dd, 2H, J=8.6 Hz, 1.6 Hz), 7.46(s, 2H), 7.94(d, 2H, J=8.6 Hz).

m/z (EI): 616 [M$^+$].

PREPARATION EXAMPLE 21

Synthesis of Ethyl 3-(6,7,8-Trimethoxynaphthalen-2-yl)propenoate 6,7,8-Trimethoxynaphthalene-2-carboaldehyde (985 mg) and ethyl diethylphosphonoacetate (1.05 mL) were treated in the same manner as in Preparation Example 17 to obtain the title compound.

Yield: 1.33 g (theoretical amount).

$^1$H-NMR (400 MHz, CDCl$_3$) δ: 1.36(t, 3H, J=7.0 Hz), 3.97(s, 3H), 3.99(s, 3H), 4.07(s, 3H), 4.29(q, 2H, J=7.0 Hz), 6.52(d, 1H, J=15.8 Hz), 6.94(s, 1H), 7.58(dd, 1H, J=12.6 Hz, 1.7 Hz), 7.67(d, 1H, J=12.6 Hz), 7.84(d, 1H, J=15.8 Hz), 8.15(br, 1H).

PREPARATION EXAMPLE 22

Synthesis of Ethyl 3-(6,7,8-Trimethoxynaphthalen-2-yl)propionate

Ethyl 3-(6,7,8-trimethoxynaphthalen-2-yl)propenoate (1.33 g) was treated in the same manner as in Preparation Example 18 to obtain the title compound.

Yield: 1.04 g (82%).

$^1$H-NMR (400 MHz, CDCl$_3$) δ: 1.25(t, 3H, J=7.1 Hz), 2.70(t, 2H, J=7.6 Hz), 3.10(t, 2H, J=7.6 Hz), 3.96(s, 3H), 3.97(s, 3H), 4.04(s, 3H), 4.14(q, 2H, J=7.1 Hz), 6.92(s, 1H), 7.26(dd, 1H, J=8.3 Hz, 1.7 Hz), 7.62(d, 1H, J=12.6 Hz), 7.84(br, 1H).

PREPARATION EXAMPLE 23

Synthesis of 2-(3-hydroxypropyl)-6,7,8-trimethoxynaphthalene

Ethyl 3-(6,7,8-trimethoxynaphthalen-2-yl)propionate (1.04 g) was treated in the same manner as in Preparation Example 3 to obtain the title compound.

Yield: 860 mg (95%).

$^1$H-NMR (400 MHz, CDCl$_3$) δ: 1,98(quint, 2H, J=8.1 Hz), 2.86(t, 2H, J=8.1 Hz), 3.66–3.74(m, 2H), 3.96(s, 3H), 3.97(s, 3H), 4.05(s, 3H), 6.93(s, 1H), 7.26(dd, 1H, J=8.3 Hz, 1.7 Hz), 7.62(d, 1H, J=8.3 Hz), 7.84(br, 1H).

PREPARATION EXAMPLE 24

Synthesis of 2-(3-methanesulfonyloxypropyl)-6,7,8-trimethoxynaphthalene 2-(3-Hydroxypropyl)-6,7,8-trimethoxynaphthalene (720 mg) was treated in the same manner as in Preparation Example 12 to obtain the title compound.

Yield: 922 mg (theoretical amount).

$^1$H-NMR (400 MHz, CDCl$_3$) δ: 2.16(quint, 2H, J=7.2 Hz), 2.84(s, 3H), 2.90(t, 2H, J=7.2 Hz), 3.97(s, 6H), 4.05(s, 3H), 4.26(t, 2H, J=7.2 Hz), 6.93(s, 1H), 7.23(dd, 1H, J=8.6 Hz, 1.7 Hz), 7.64(d, 1H, J=8.6 Hz), 7.83(br, 1H).

EXAMPLE 11

Synthesis of N,N'-bis[3-(6,7,8-trimethoxynaphthalen-2-yl)propyl]homopiperazine

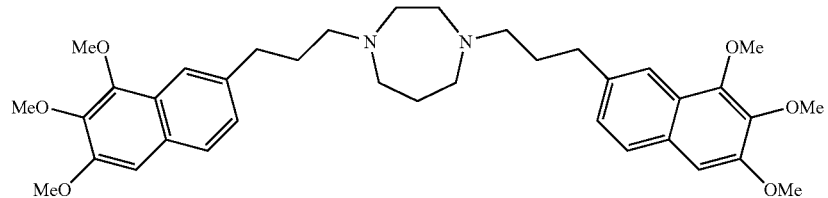

2-(3-Methanesulfonyloxypropyl)-6,7,8-trimethoxynaphthalene (479 mg) and homopiperazine (67 mg) were reacted in the same manner in Example 1 to obtain the title compound as a free base.

Yield: 282 mg (69%).

$^1$H-NMR (400 MHz, CDCl$_3$) δ: 1.82–1.96(m, 6H), 2.57(t, 4H, J=7.6 Hz), 2.72–2.82(m, 12H), 3.96(s, 6H), 3.96(s, 6H), 4.04(s, 6H), 6.92(s, 2H), 7.24(dd, 2H, J=8.4 Hz, 1.8 Hz), 7.61(d, 2H, J=8.4 Hz), 7.81(s, 2H).

m/z (EI): 616[M$^+$].

PREPARATION EXAMPLE 25

Synthesis of 2-methyl-5,6,7-trimethoxyquinoline

A 6 M hydrochloric acid solution (20 mL) of 3,4,5-trimethoxyaniline (3.1 g) was heated to 100° C., to which crotonaldehyde (1.5 mL) was slowly added dropwise. The mixture was stirred for 3.5 hours as it is. After allowing the reaction mixture to cool, it was washed with ether, and the resultant water layer was alkalified with a potassium carbonate solution. After extracted with ethyl acetate, the resultant organic layer was washed with water and saturated brine and dried over anhydrous magnesium sulfate. The organic layer was concentrated under reduced pressure, and the residue was then purified by column chromatography on silica gel (ethyl acetate:hexane=1:2 to 1:1) to obtain the title compound.

Yield: 1.98 g (50%).

$^1$H-NMR (400 MHz, CDCl$_3$) δ: 2.69(s, 3H), 3.97(s, 3H), 3.99(s, 3H), 4.05(s, 3H), 7.15(d, 1H, J=8.3 Hz), 7.19(s, 1H), 8.24(d, 1H, J=8.3 Hz)

PREPARATION EXAMPLE 26

Synthesis of 5,6,7-trimethoxyquinoline-2-carboaldehyde

Selenium dioxide (980 mg) was suspended in a mixed solvent of dioxane (12 mL) and water (0.5 mL), and the suspension was heated to 45° C. A solution of 2-methyl-5,6,7-trimethoxyquinoline (1.97 g) in dioxane (3 mL) was slowly added dropwise thereto, and the mixture was heated to 105° C. and stirred for 1.5 hours. After allowing the reaction mixture to room temperature, selenium dioxide was filtered, and the filtrate was concentrated and purified by column chromatography on silica gel (ethyl acetate:hexane=1:4) to obtain the title compound.

Yield: 1.40 g (67%).

$^1$H-NMR (400 MHz, CDCl$_3$) δ: 4.04(s, 3H), 4.06(s, 3H), 4.08(s, 3H), 7.38(s, 1H), 7.91(d, 1H, J=8.6 Hz), 8.51(dt, 1H, J=8.6 Hz, 0.3 Hz), 10.18(d, 1H, J=0.7 Hz).

PREPARATION EXAMPLE 27

Synthesis of 2-hydroxymethyl-5,6,7-trimethoxyquinoline

Sodium borohydride (418 mg) and 5,6,7-trimethoxyquinoline-2-carboaldehyde (2.14 g) were successively added to a mixed solvent of methanol (30 mL) and THF (30 mL) under ice cooling, and the mixture was stirred at room temperature for 1 hour. The reaction mixture was concentrated under reduced pressure, and the residue was then extracted with ethyl acetate. The resultant organic layer was washed with water and saturated brine, and dried over anhydrous magnesium sulfate. After concentrating the organic layer under reduced pressure, the residue was purified by column chromatography on silica gel (chloroform:methanol=30:1) to obtain the title compound.

Yield: 1.45 g (theoretical amount).

$^1$H-NMR (400 MHz, CDCl$_3$) δ: 3.98(s, 3H), 4.02(s, 3H), 4.07(s, 3H), 4.28(br, 1H), 4.87(s, 2H), 7.16(d, 1H, J=8.6 Hz), 7.23(s, 1H), 8.33(d, 1H, J=8.6 Hz).

PREPARATION EXAMPLE 28

Synthesis of 2-chloromethyl-5,6,7-trimethoxyquinoline

Thionyl chloride (1.7 mL) was added to a solution of 2-hydroxymethyl-5,6,7-trimethoxyquinoline (1.45 g) in dichloromethane (15 mL) under ice cooling, and the mixture was stirred at room temperature for 30 minutes. After concentrating the reaction mixture under reduced pressure, an aqueous solution of potassium carbonate was added to the residue to alkalify it. The thus-treated residue was extracted with diethyl ether. The resultant organic layer was washed with water and saturated brine, dried over anhydrous magnesium sulfate and then concentrated under reduced pressure, and the residue was purified by column chromatography on silica gel (ethyl acetate:hexane=1:2) to obtain the title compound.

Yield: 1.34 g (88%).

$^1$H-NMR (400 MHz, CDCl$_3$) δ: 3.99(s, 3H), 4.01(s, 3H), 4.06(s, 3H), 4.79(s, 2H), 7.23(s, 1H), 7.45(d, 1H, J=8.6 Hz), 8.39(d, 1H, J=8.6 Hz).

EXAMPLE 12

Synthesis of N,N'-bis[(5,6,7-trimethoxyquinolin-2-yl)methyl]piperazine

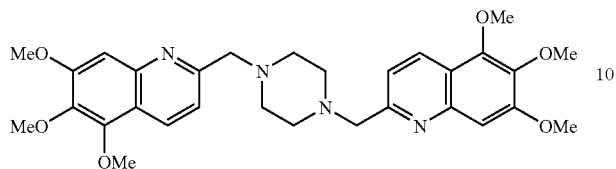

2-Chloromethyl-5,6,7-trimethoxyquinoline (400 mg) and piperazine (65 mg) were reacted in the same manner as in Example 1 to obtain the title compound as a free base.
Yield: 400 mg (97%).
$^1$H-NMR (400 MHz, CDCl$_3$) δ: 3.77(br, 8H), 3.80(s, 4H), 3.97(s, 6H), 3.99(s, 6H), 4.05(s, 6H), 7.24(s, 2H), 7.48(d, 2H, J=8.5 Hz), 8.31(d, 2H, J=8.5 Hz).
m/z (EI): 548 [M$^+$].

EXAMPLE 13

Synthesis of N,N'-bis[(5,6,7-trimethoxyquinolin-2-yl)methyl]homopiperazine

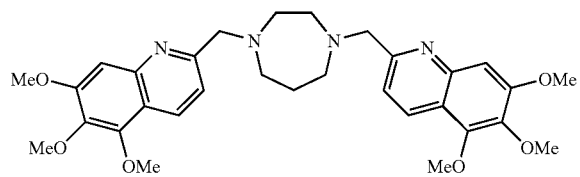

2-Chloromethyl-5,6,7-trimethoxyquinoline (400 mg) and homopiperazine (765 mg) were reacted in the same manner as in Example 1 to obtain the title compound as a free base.
Yield: 331 mg (78%).
$^1$H-NMR (400 MHz, CDCl$_3$) δ: 1.88(br, 2H), 2.75–2.79 (m, 8H), 3.95(s, 4H), 3.97(s, 6H), 3.99(s, 6H), 4.06(s, 6H), 7.22(s, 2H), 7.56(d, 2H, J=8.5 Hz), 8.32(d, 2H, J=8.5 Hz).
m/z (EI): 562 [M$^+$].

PREPARATION EXAMPLE 29

Synthesis of 2-methyl-6,7,8-trimethoxyquinoline 2,3,4-Trimethoxyaniline (5.2 g) was treated in the same manner as in Preparation Example 25 to obtain the title compound.
Yield: 4.2 g (67%).
$^1$H-NMR (400 MHz, CDCl$_3$) δ: 2.73(s, 3H), 3.97(s, 3H), 4.03(s, 3H), 4.17(s, 3H), 6.83(s, 1H), 7.18(d, 1H, J=8.4 Hz), 7.88(d, 1H, J=8.4 Hz).

PREPARATION EXAMPLE 30

Synthesis of 6,7,8-trimethoxyquinoline-2-carboaldehyde

2-Methyl-6,7,8-trimethoxyquinoline (4.2 g) was treated in the same manner as in Preparation Example 26 to obtain the title compound.

Yield: 2.37 g (51%).
$^1$H-NMR (400 MHz, CDCl$_3$) δ: 4.04(s, 3H), 4.08(s, 3H), 4.23(s, 3H), 6.94(s, 1H), 7.96(d, 1H, J=8.3 Hz), 8.13(dt, 1H, J=8.3 Hz, 0.5 Hz), 10.17(s, 1H).

PREPARATION EXAMPLE 31

Synthesis of 2-chloromethyl-6,7,8-trimethoxyquinoline 6,7,8-Trimethoxyquinoline-2-carboaldehyde (742 mg) was treated in the same manner as in Preparation Example 27 and Preparation Example 28 to obtain the title compound.
Yield: 714 mg (89%).
$^1$H-NMR (400 MHz, CDCl$_3$) δ: 3.99(s, 3H), 4.04(s, 3H), 4.18(s, 3H), 4.86(s, 2H), 6.87(s, 1H), 7.53(d, 1H, J=8.4 Hz), 8.04(d, 1H, J=8.4 Hz).

EXAMPLE 14

Synthesis of N,N'-bis[(6,7,8-trimethoxyquinolin-2-yl)methyl]piperazine

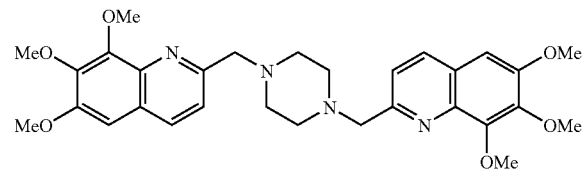

2-Chloromethyl-6,7,8-trimethoxyquinoline (336 mg) and piperazine (54 mg) were reacted in the same manner as in Example 1 to obtain the title compound as a free base.
Yield: 330 mg (theoretical amount).
$^1$H-NMR (400 MHz, CDCl$_3$) δ: 2.63(br, 8H), 3.88(s, 4H), 3.97(s, 6H), 4.03(s, 6H), 4.16(s, 6H), 6.85(s, 2H), 7.54(d, 2H, J=8.4 Hz), 7.96(d, 2H, J=8.4 Hz).
m/z (EI): 548 [M$^+$].

EXAMPLE 15

Synthesis of N,N'-bis[(6,7,8-trimethoxyquinolin-2-yl)methyl]homopiperazine

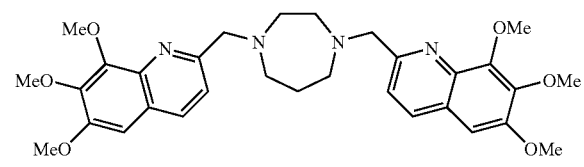

2-Chloromethyl-6,7,8-trimethoxyquinoline (350 mg) and homopiperazine (65 mg) were reacted in the same manner as in Example 1 to obtain the title compound as a free base.
Yield: 241 mg (66%).
$^1$H-NMR (400 MHz, CDCl$_3$) δ: 1.86(br, 2H), 2.82(br, 4H), 2.87(t, 4H, J=5.9 Hz), 3.97(s, 4H), 4.01(s, 6H), 4.03(s, 6H), 4.16(s, 6H), 6.85(s, 2H), 7.62(d, 2H, J=8.4 Hz), 7.97(d, 2H, J=8.4 Hz).
m/z (EI): 562 [M$^+$].

PREPARATION EXAMPLE 32

Synthesis of N-(6-formyl-3,4,5-trimethoxyphenyl)-chloroacetamide

6-Nitro-2,3,4-trimethoxybenzaldehyde (4.0 g) was dissolved in methanol (40 mL) and THF (20 mL), 10% palladium on carbon was added to the solution, and the mixture was stirred at room temperature for 5 hours under a hydrogen atmosphere. After the catalyst was removed by filtration, the filtrate was concentrated under reduced pressure, and the residue was purified by column chromatography on silica gel (ethyl acetate:hexane=1:4 to 1:3) to obtain 6-amino-2,3,4-trimethoxybenzaldehyde (3.1 g). This product was immediately dissolved in dichloromethane (35 mL), and triethylamine (4.2 mL) was added thereto. Chloroacetyl chloride (1.78 mL) was added dropwise under ice cooling, and the mixture was stirred overnight at room temperature. The reaction mixture was extracted with chloroform, and the extract was washed with water and saturated brine, and dried over anhydrous magnesium sulfate. After concentrating the extract under reduced pressure, the residue was purified by column chromatography on silica gel (ethyl acetate:hexane=1:4 to 1:3) to obtain the title compound.

Yield: 2.74 g (58%).
$^1$H-NMR (400 MHz, CDCl$_3$) δ: 3.85(s, 3H), 3.98(s, 3H), 4.04(s, 3H), 4.18(s, 2H), 8.23(s, 1H), 10.24(s, 1H).

PREPARATION EXAMPLE 33

Synthesis of 2-chloromethyl-5,6,7-trimethoxy-1,3-quinazoline

N-(6-Formyl-3,4,5-trimethoxyphenyl)chloroacetamide (3.36 g) was dissolved in methanol (60 mL) and THF (10 mL) which were saturated with ammonia gas, and the solution was stirred at room temperature for 8 hours. The reaction mixture was concentrated under reduced pressure, and the residue was then purified by column chromatography on silica gel (ethyl acetate:hexane=1:3 to 1:2) to obtain the title compound.

Yield: 1.32 g (42%).
$^1$H-NMR (400 MHz, CDCl$_3$) δ: 3.98(s, 3H), 4.04(s, 3H), 4.15(s, 3H), 4.85(s, 2H), 7.14(s, 1H), 9.46(s, 1H).

EXAMPLE 16

Synthesis of N,N'-bis[(5,6,7-trimethoxy-1,3-quinazolin-2-yl)methyl]piperazine

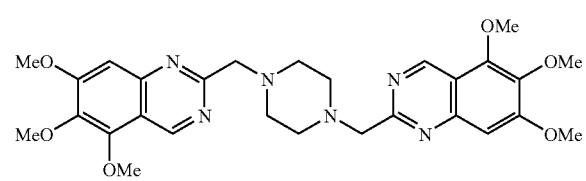

2-Chloromethyl-5,6,7-trimethoxy-1,3-quinazoline (250 mg) and piperazine (40 mg) were reacted in the same manner as in Example 1 to obtain the title compound as a free base.

Yield: 172 mg (67%).

$^1$H-NMR (400 MHz, CDCl$_3$) δ: 2.68(br, 8H), 3.86(s, 4H), 3.89(s, 6H), 3.94(s, 6H), 4.05(s, 6H), 7.07(s, 2H), 9.38(s, 2H).
m/z (EI): 550 [M$^+$].

EXAMPLE 17

Synthesis of N,N'-bis[(5,6,7-trimethoxy-1,3-quinazolin-2-yl)methyl]homopiperazine

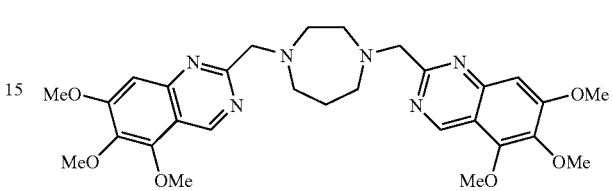

2-Chloromethyl-5,6,7-trimethoxy-1,3-quinazoline (280 mg) and homopiperazine (52 mg) were reacted in the same manner as in Example 1 to obtain the title compound as a free base.

Yield: 220 mg (75%).
$^1$H-NMR (400 MHz, CDCl$_3$) δ: 1.91(br, 2H), 2.92–3.01 (m, 8H), 3.96(s, 6H), 4.02(s, 6H), 4.07(s, 4H), 4.13(s, 6H), 7.13(s, 2H), 9.45(s, 2H).
m/z (EI): 564 [M$^+$].

PREPARATION EXAMPLE 34

Synthesis of Methyl 3-(3,4,5-trimethoxyphenyl)-2-azidopropenoate 3,4,5-Trimethoxybenzaldehyde (992 mg) and methyl azidoacetate (2.91 g) were dissolved in dry methanol (2 mL), and a dry methanol solution (10 mL) of sodium (582 mg) was added dropwise to the solution at 0° C. over 2 hours under an argon atmosphere. After stirring the reaction mixture for 30 minutes as it is, it was concentrated under reduced pressure, and water was added to the residue to collect crystals deposited by filtration. The crystals were washed with water and dried to obtain the title compound.

Yield: 1.2 g (81%).

PREPARATION EXAMPLE 35

Synthesis of Methyl 5,6,7-trimethoxyindole-2-carboxylate

Xylene (15 mL) was placed in a three-necked flask and stirred under reflux, and a xylene solution (30 mL) of methyl 3-(3,4,5-trimethoxyphenyl)-2-azidopropenoate (1.2 g) was added dropwise over 3 hours. The reaction mixture was refluxed for 1 hour and concentrated under reduced pressure. Water was added to the residue to conduct extraction with ethyl acetate. The extract was washed with water and saturated brine, dried over anhydrous magnesium sulfate and then concentrated under reduced pressure. The residue was purified by column chromatography on silica gel (ethyl acetate:hexane=1:3) to obtain the title compound.

Yield: 960 mg (88%).
$^1$H-NMR (400 MHz, CDCl$_3$) δ: 3.90(s, 3H), 3.93(s, 6H), 4.07(s, 3H), 6.82(s, 1H), 7.10(d, 1H, J=2.3 Hz), 8.88(br, 1H).

PREPARATION EXAMPLE 36

Synthesis of 5,6,7-trimethoxyindole-2-carboxylic acid

Methyl 5,6,7-trimethoxyindole-2-carboxylate (700 mg) was dissolved in methanol (13 mL), potassium hydroxide powder (450 mg) was added to the solution, and the mixture was stirred for 3 hours under reflux. After allowing the reaction mixture to cool, it was concentrated under reduced pressure, and water was added to the residue. The resultant water layer was washed with ether and then neutralized with diluted hydrochloric acid. Crystals deposited were collected by filtration and dried to obtain the title compound.

Yield: 604 mg (92%).

$^1$H-NMR (400 MHz, CDCl$_3$) δ: 3.90(s, 3H), 3.93(s, 3H), 4.07(s, 3H), 6.85(s, 1H), 7.13(s, 1H), 9.79(br, 1H).

PREPARATION EXAMPLE 37

Synthesis of N,N'-bis(5,6,7-trimethoxyindole-2-carbonyl)piperazine 5,6,7-Trimethoxyindole-2-carboxylic acid (300 mg) and piperazine (52 mg) were dissolved in dichloromethane (5 mL), and water-soluble carbodiimide hydrochloride (232 mg) and N,N-dimethylaminopyridine (10 mg) were added to the solution. The mixture was stirred overnight at room temperature. The reaction mixture was poured into water and extracted with chloroform. The extract was successively washed with diluted hydrochloric acid, a dilute aqueous solution of sodium hydroxide, water and saturated brine, dried over anhydrous magnesium sulfate and then concentrated under reduced pressure. The residue was purified by preparative TLC on silica gel (ethyl acetate:hexane=1:1) to obtain the title compound.

Yield: 310 mg (theoretical amount).

EXAMPLE 18

Synthesis of N,N'-bis[(5,6,7-trimethoxyindol-2-yl)-methyl]piperazine

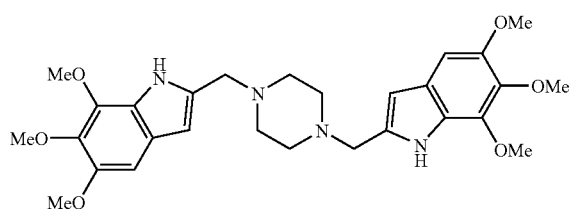

N,N'-Bis(5,6,7-trimethoxyindole-2-carbonyl)-piperazine (148 mg) was dissolved in THF (5 mL), and lithium aluminum hydride (10 mg) was gradually added to the solution under ice cooling. The mixture was warmed to room temperature and stirred for 6 hours, and sodium sulfate decahydrate was added thereto. After filtration, the filtrate was concentrated under reduced pressure and purified by column chromatography on silica gel (chloroform:methanol=20:1) to obtain the title compound as a free base.

Yield: 107 mg (79%).

$^1$H-NMR (400 MHz, CDCl$_3$) δ: 2.51(br, 8H), 3.63(s, 4H), 3.88(s, 6H), 3.90(s, 6H), 4.07(s, 6H), 6.24(s, 2H), 6.76(s, 2H), 8.44(s, 2H).

m/z: 524 [M$^+$].

PREPARATION EXAMPLE 38

Synthesis of N,N'-bis(5,6,7-trimethoxyindole-2-carbonyl)homopiperazine 5,6,7-Trimethoxyindole-2-carboxylic acid (300 mg) and homopiperazine (60 mg) were reacted in the same manner as in Preparation Example 37 to obtain the title compound.

Yield: 309 mg (92%).

$^1$H-NMR (400 MHz, CDCl$_3$) δ: 3.90(s, 3H), 3.93(s, 3H), 4.07(s, 3H), 6.82(s, 1H), 7.10(s, 1H), 8.88(br, 1H).

EXAMPLE 19

Synthesis of N,N'-bis[(5,6,7-trimethoxyindol-2-yl)-methyl]homopiperazine

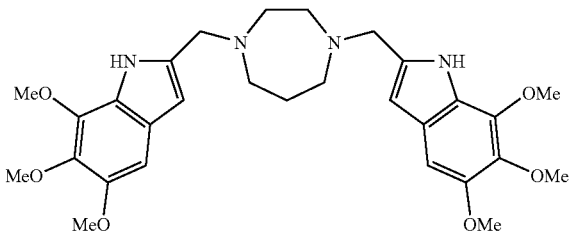

N,N'-Bis(5,6,7-trimethoxyindole-2-carbonyl)-homopiperazine (148 mg) was treated in the same manner as in Example 18 to obtain the title compound as a free base.

Yield: 59 mg (21%).

$^1$H-NMR (400 MHz, CDCl$_3$) δ: 1.83(br, 2H), 2.75(br, 4H), 2.78(t, 4H, J=5.9 Hz), 3.78(s, 4H), 3.88(s, 6H), 3.90(s, 6H), 4.06(s, 6H), 6.23(s, 2H), 6.76(s, 2H), 8.91(br, 2H).

m/z (EI): 538 [M$^+$].

PREPARATION EXAMPLE 39

Synthesis of Methyl 3-(2,3,4-trimethoxyphenyl)-2-azidopropenoate 2,3,4-Trimethoxybenzaldehyde (6.1 g) was treated in the same manner as in Preparation Example 34 to obtain the title compound.

Yield: 8.05 g (88%).

PREPARATION EXAMPLE 40

Synthesis of Methyl 4,5,6-trimethoxyindole-2-carboxylate

Methyl 3-(2,3,4-trimethoxyphenyl)-2-azidopropenoate (8.0 g) was treated in the same manner as in Preparation Example 35 to obtain the title compound.

Yield: 5.74 g (80%).

$^1$H-NMR (400 MHz, CDCl$_3$) δ: 3.87(s, 3H), 3.90(s, 3H), 3.92(s, 3H), 4.12(s, 3H), 6.59(d, 1H, J=0.6 Hz), 7.28(dd, 1H, J=2.2 Hz, 0.6 Hz), 8.78(br, 1H).

PREPARATION EXAMPLE 41

Synthesis of 4,5,6-trimethoxyindole-2-carboxylic acid

Methyl 4,5,6-trimethoxyindole-2-carboxylate (700 mg) was treated in the same manner as in Preparation Example 36 to obtain the title compound.

Yield: 592 mg (89%).
$^1$H-NMR (400 MHz, CDCl$_3$) δ: 3.69(s, 3H), 3.80(s, 3H), 4.00(s, 3H), 6.64(s, 1H), 7.05(d, 1H, J=2.3 Hz), 11.57(br, 1H).

PREPARATION EXAMPLE 42

Synthesis of N,N'-bis(4,5,6-trimethoxyindole-2-carbonyl)piperazine 4,5,6-Trimethoxyindole-2-carboxylic acid (290 mg) and piperazine (50 mg) were reacted in the same manner as in Preparation Example 37 to obtain the title compound.
Yield: 160 mg (53%).

EXAMPLE 20

Synthesis of N,N'-bis[(4,5,6-trimethoxyindol-2-yl)-methyl]piperazine

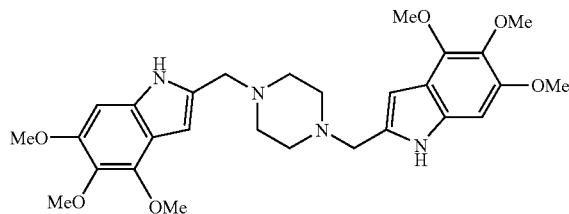

N,N'-bis(4,5,6-trimethoxyindole-2-carbonyl)-piperazine (100 mg) was treated in the same manner as in Example 18 to obtain the title compound as a free base.
Yield: 36 mg (38%).
$^1$H-NMR (400 MHz, CDCl$_3$) δ: 2.58(br, 8H), 3.61(s, 4H), 3.66(s, 6H), 3.88(s, 6H), 4.09(s, 6H), 6.38(s, 2H), 6.61(s, 2H), 8.40(br, 2H).
m/z (EI): 524 [M$^+$].

PREPARATION EXAMPLE 43

Synthesis of N,N'-bis(4,5,6-trimethoxyindole-2-carbonyl)homopiperazine 4,5,6-Trimethoxyindole-2-carboxylic acid (290 mg) and homopiperazine (58 mg) were reacted in the same manner as in Preparation Example 37 to obtain the title compound.
Yield: 182 mg (58%).

EXAMPLE 21

Synthesis of N,N'-bis[(4,5,6-trimethoxyindol-2-yl)-methyl]homopiperazine

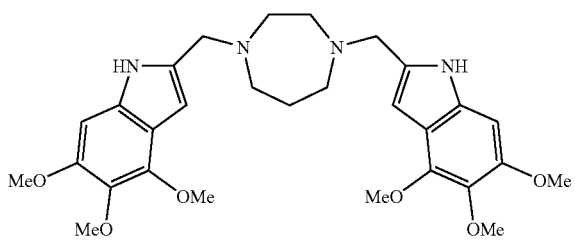

N,N'-bis(4,5,6-trimethoxyindole-2-carbonyl)-homopiperazine (170 mg) was treated in the same manner as in Example 18 to obtain the title compound as a free base.
Yield: 78 mg (48%).

$^1$H-NMR (400 MHz, CDCl$_3$) δ: 1.83(br, 2H), 2.76(br, 4H), 2.80(t, 4H, J=5.9 Hz), 3.79(s, 4H), 3.86(s, 6H), 3.88(s, 6H), 4.08(s, 6H), 6.37(s, 2H), 6.65(s, 2H), 9.21(br, 2H).
m/z (EI): 538 [M$^+$].

PREPARATION EXAMPLE 44

Synthesis of Methyl N-methyl-4,5,6-trimethoxyindole-2-carboxylate

Methyl 3-(2,3,4-trimethoxyphenyl)-2-azidopropenoate (799 mg), potassium tert-butoxide (438 mg) and 18-crown-6(71 mg) were dissolved in dry benzene (60 mL), and the solution was stirred for 15 minutes. Iodomethane (0.28 mL) was then added, and the mixture was stirred overnight. Water was added to the reaction mixture to conduct extraction with ethyl acetate. The resultant organic layer was washed with water and saturated brine, dried over anhydrous magnesium sulfate and then concentrated under reduced pressure to obtain the title compound.
Yield: 768 mg (91%).
$^1$H-NMR (400 MHz, CDCl$_3$) δ: 3.87(s, 3H), 3.89(s, 3H), 3.95(s, 3H), 4.01(s, 3H), 4.12(s, 3H), 6.50(s, 1H), 7.36(s, 1H).

PREPARATION EXAMPLE 45

Synthesis of N-methyl-4,5,6-trimethoxyindole-2-carboxylic acid

Methyl N-methyl-4,5,6-trimethoxyindole-2-carboxylate (190 mg) was treated in the same manner as in Preparation Example 36 to obtain the title compound.
Yield: 134 mg (78%).
$^1$H-NMR (400 MHz, CDCl$_3$) δ: 3.87(s, 3H), 3.96(s, 3H), 4.02(s, 3H), 4.14(s, 3H), 6.49(s, 1H), 7.51(s, 1H).

PREPARATION EXAMPLE 46

Synthesis of N,N'-bis(1-methyl-4,5,6-trimethoxyindole-2-carbonyl)piperazine

N-Methyl-4,5,6-trimethoxyindole-2-carboxylic acid (200 mg) and piperazine (35 mg) were reacted in the same manner as in Preparation Example 37 to obtain the title compound.
Yield: 200 mg (93%).
$^1$H-NMR (400 MHz, CDCl$_3$) δ: 3.81(s, 6H), 3.87(s, 6H), 3.89(br, 8H), 3.95(s, 6H), 4.09(s, 6H), 6.53(s, 2H), 6.69(s, 2H).

EXAMPLE 22

Synthesis of N,N'-bis[(1-methyl-4,5,6-trimethoxyindol-2-yl)methyl]piperazine

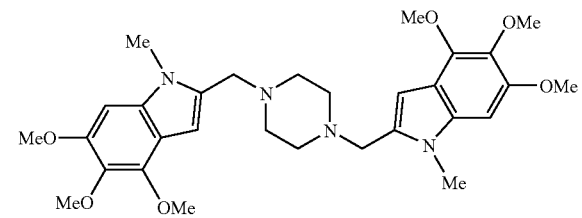

N,N'-bis(1-methyl-4,5,6-trimethoxyindole-2-carbonyl)piperazine (145 mg) was treated in the same manner as in Example 18 to obtain the title compound.

Yield: 94 mg (68%).

$^1$H-NMR (400 MHz, CDCl$_3$) δ: 2.44(br, 8H), 3.56(s, 4H), 3.71(s, 6H), 3.86(s, 6H), 3.93(s, 6H), 4.08(s, 6H), 6.37(s, 2H), 6.52(s, 2H).

m/z (EI): 552 [M$^+$].

PREPARATION EXAMPLE 47

Synthesis of N,N'-bis(1-methyl-4,5,6-trimethoxyindole-2-carbonyl)homopiperazine N-Methyl-4,5,6-trimethoxyindole-2-carboxylic acid (130 mg) and homopiperazine (24 mg) were reacted in the same manner as in Preparation Example 37 to obtain the title compound.

Yield: 165 mg (theoretical amount).

$^1$H-NMR (400 MHz, CDCl$_3$) δ: 2.06(br, 2H), 3.75(s, 6H), 3.86(s, 6H), 3.93(s, 6H), 3.82–4.00(m, 4H), 4.07(br, 4H), 6.50 (s, 2H), 6.69(br, 2H).

EXAMPLE 23

Synthesis of N,N'-bis[(1-methyl-4,5,6-trimethoxyindol-2-yl)methyl]homopiperazine

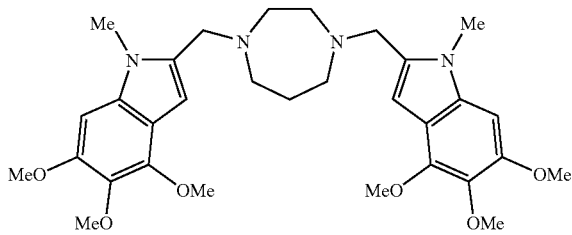

N,N'-bis(1-methyl-4,5,6-trimethoxyindole-2-carbonyl)homopiperazine (145 mg) was treated in the same manner as in Example 18 to obtain the title compound.

Yield: 107 mg (79%).

$^1$H-NMR (400 MHz, CDCl$_3$) δ: 1.76(br, 2H), 2.63(s, 4H), 2.70(t, 4H, J=5,9 Hz), 3.67(s, 4H), 3.74(s, 6H), 3.86(s, 6H), 3.93(s, 6H), 4.09(s, 6H), 6.34(s, 2H), 6.52(s, 2H).

m/z (EI): 566 [M$^+$].

PREPARATION EXAMPLE 48

Synthesis of Methyl 1-phenyl-4,5,6-trimethoxyindole-2-carboxylate

Methyl 4,5,6-trimethoxyindole-2-carboxylate (533 mg), bromobenzene (0.22 mL), copper oxide (64 mg) and potassium hydroxide (336 mg) were suspended in dry DMF (10 mL), and the suspension was refluxed and stirred for 6 hours under an argon atmosphere. After cooling, the reaction mixture was dissolved in water (100 mL) and filtered through celite. The filtrate was extracted with ethyl acetate, and the extract was washed with water and saturated brine, dried over anhydrous magnesium sulfate and then concentrated under reduced pressure. The residue was dissolved in methanol (20 mL) and chloroform (20 mL), and water-soluble carbodiimide hydrochloride (192 mg) and N,N-dimethylaminopyridine (small amount) were added to the solution. The mixture was stirred overnight at room temperature. After concentrating the reaction mixture under reduced pressure, water was added to the residue to conduct extraction with ethyl acetate. The resultant organic layer was washed with water and saturated brine, dried over anhydrous magnesium sulfate and then concentrated under reduced pressure. The residue was purified by preparative TLC on silica gel (ethyl acetate:hexane=1:3) to obtain the title compound.

Yield: 220 mg (35%).

$^1$H-NMR (400 MHz, CDCl$_3$) δ: 3.75(s, 3H), 3.76(s, 3H), 3.87(s, 3H), 4.16(s, 3H), 6.20(s, 1H), 7.30–7.55(m, 5H), 7.60(s, 1H).

PREPARATION EXAMPLE 49

Synthesis of 1-phenyl-4,5,6-trimethoxyindole-2-carboxylic acid

Methyl 1-phenyl-5,6,7-trimethoxyindole-2-carboxylate (280 mg) was dissolved in ethanol (5 mL), a 10% aqueous solution (2 mL) of potassium hydroxide was added to the solution, and the mixture was stirred for 30 minutes under reflux. After cooling, the reaction mixture was concentrated under reduced pressure, and the residue was dissolved in water and washed with ether. The water layer was then neutralized with hydrochloric acid and extracted with ethyl acetate. The resultant organic layer was washed with water and saturated brine, dried over anhydrous magnesium sulfate and then concentrated under reduced pressure to obtain the title compound.

Yield: 193 mg (72%).

$^1$H-NMR (400 MHz, CDCl$_3$) δ: 3.75(s, 3H), 3.87(s, 3H), 4.16(s, 3H), 6.19(s, 1H), 7.29–7.35(m, 2H), 7.44–7.55(m, 3H), 7.60(s, 1H).

PREPARATION EXAMPLE 50

Synthesis of N,N'-bis(1-phenyl-4,5,6-trimethoxyindole-2-carbonyl)homopiperazine 1-Phenyl-4,5,6-trimethoxyindole-2-carboxylic acid (91 mg) and homopiperazine (14 mg) were reacted in the same manner as in Preparation Example 37 to obtain the title compound.

Yield: 100 mg (99%).

$^1$H-NMR (400 MHz, CDCl$_3$) δ: 1.51(br, 2H), 3.35–3.65 (br, 8H), 3.79(s, 6H), 3.88(s, 6H), 4.10(s, 6H), 6.48(s, 2H), 6.78(s, 2H), 7.32–7.54(m, 10H)

EXAMPLE 24

Synthesis of N,N'-bis[(1-phenyl-4,5,6-trimethoxyindol-2-yl)methyl]homopiperazine

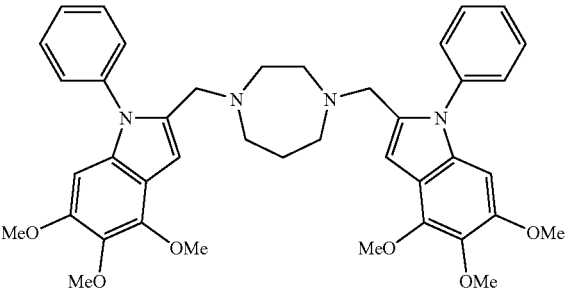

N,N'-bis(1-phenyl-4,5,6-trimethoxyindole-2-carbonyl)homopiperazine (99 mg) was treated in the same manner as in Example 18 to obtain the title compound as a free base.

Yield: 81 mg (84%).
$^1$H-NMR (400 MHz, CDCl$_3$) δ: 1.51(br, 2H), 2.38(s, 4H), 2.44(t, 4H, J=6.1 Hz), 3.45(s, 4H), 3.75(s, 6H), 3.87(s, 6H), 4.13(s, 6H), 6.35(s, 2H), 7.52(s, 2H), 7.36–7.49(m, 10H). m/z (EI): 690 [M$^+$].

PREPARATION EXAMPLE 51

Synthesis of 2-hydroxymethyl-1-methyl-4,5,6-trimethoxyindole

Methyl 1-methyl-4,5,6-trimethoxyindole-2-carboxylate (1.17 g) was dissolved in dry THF under an argon atmosphere at 0° C., a 1 M toluene solution (13.2 mL) of diisopropylaluminum hydride was added dropwise to the solution, and the mixture was stirred for 1 hour as it is. The reaction mixture was diluted with ether, the sodium sulfate decahydrate was added thereto, and the mixture was stirred further for 1 hour. After the reaction mixture was filtered, and the filtrate was concentrated, the residue was purified by column chromatography on silica gel (ethyl acetate:hexane=1:2 to 1:1) to obtain the title compound.
Yield: 861 mg (78%).
$^1$H-NMR (400 MHz, CDCl$_3$) δ: 3.36(s, 3H), 3.89(s, 3H), 3.90(s, 3H), 4.06(s, 3H), 4.79(s, 2H), 6.31(d, 1H, J=2.3 Hz), 6.78(s, 1H), 8.39(br, 1H).

PREPARATION EXAMPLE 52

Synthesis of 1-methyl-4,5,6-trimethoxyindole-2-carboaldehyde

2-Hydroxymethyl-1-methyl-4,5,6-trimethoxyindole (861 mg) was dissolved in benzene (50 mL), activated manganese dioxide (8.7 g) was added to the solution, and the mixture was stirred at room temperature for 2 hours. After the reaction mixture was filtered, and the filtrate was concentrated, the residue was purified by column chromatography on silica gel (ethyl acetate:hexane=1:2) to obtain the title compound.
Yield: 769 mg (90%).
$^1$H-NMR (400 MHz, CDCl$_3$) δ: 3.80(s, 3H), 3.92(s, 3H), 3.95(s, 3H), 4.06(s, 3H), 6.59(s, 1H), 7.70(s, 1H), 10.30(s, 1H).

PREPARATION EXAMPLE 53

Synthesis of Ethyl 3-(1-methyl-4,5,6-trimethoxyindole)propenoate

1-Methyl-4,5,6-trimethoxyindole-2-carboaldehyde (250 mg) and ethyl diethylphosphonoacetate (0.3 mL) were reacted in the same manner as in Preparation Example 17 to obtain the title compound.

Yield: 254 mg (83%).
$^1$H-NMR (400 MHz, CDCl$_3$) δ: 1.34(t, 3H, J=7.1 Hz), 3.76(s, 3H), 3.86(s, 3H), 3.94(s, 3H), 4.10(s, 3H), 4.27(q, 2H, J=7.1 Hz), 6.40(d, 1H, J=15.8 Hz), 6.47(s, 1H), 7.01(s, 1H), 7.73(d, 1H, J=15.8 Hz).

PREPARATION EXAMPLE 54

Synthesis of Ethyl 3-(1-methyl-4,5,6-trimethoxyindole)propionate

Ethyl 3-(1-methyl-4,5,6-trimethoxyindole)-propenoate (254 mg) was treated in the same manner as in Preparation Example 18 to obtain the title compound.
Yield: 250 mg (98%).
$^1$H-NMR (400 MHz, CDCl$_3$) δ: 1.28(t, 3H, J=7.1 Hz), 2.75(t, 2H, J=6.1 Hz), 3.04(t, 2H, J=6.1 Hz), 3.62(s, 3H), 3.86(s, 3H), 3.92(s, 3H), 4.07(s, 3H), 4.17(q, 2H, J=7.1 Hz), 6.27(s, 1H), 6.50(s, 1H).

PREPARATION EXAMPLE 55

Synthesis of 2-(3-hydroxypropyl)-N-methyl-4,5,6-trimethoxyindole

Ethyl 3-(1-methyl-4,5,6-trimethoxyindole)propionate (160 mg) was treated in the same manner as in Preparation Example 19 to obtain the title compound.
Yield: 160 mg (71%).
$^1$H-NMR (400 MHz, CDCl$_3$) δ: 1.98(quint, 2H, J=7.6 Hz), 2.82(t, 2H, J=7.6 Hz), 3.61(s, 3H), 3.78(t, 2H, J=7.6 Hz), 3.86(s, 3H), 3.92(s, 3H), 4.08(s, 3H), 6.29(s, 1H), 6.50(s, 1H).

PREPARATION EXAMPLE 56

Synthesis of 2-(3-methanesulfonyloxypropyl)-1-methyl-4,5,6-trimethoxyindole 2-(3-Hydroxypropyl)-1-methyl-4,5,6-trimethoxyindole (160 mg) was treated in the same manner as in Preparation Example 20 to obtain the title compound.
Yield: 147 mg (72%).
$^1$H-NMR (400 MHz, CDCl$_3$) δ: 2.19(quint, 2H, J=6.0 Hz), 2.86(t, 2H, J=6.0 Hz), 3.01(s, 3H), 3.61(s, 3H), 3.86(s, 3H), 3.93(s, 3H), 4.08(s, 3H), 4.34(t, 2H, J=6.0 Hz), 6.30(s, 1H), 6.51(s, 1H).

EXAMPLE 25

Synthesis of N,N'-bis[3-(1-methyl-4,5,6-trimethoxy-indol-2-yl)propyl]piperazine

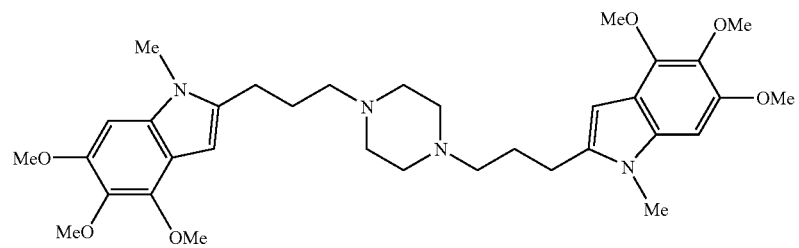

2-(3-Methanesulfonyloxypropyl)-N-methyl-4,5,6-tri-methoxyindole (160 mg) and piperazine (17 mg) were reacted in the same manner as in Example 1 to obtain the title compound as a free base.

Yield: 91 mg (75%).

$^1$H-NMR (400 MHz, CDCl$_3$) δ: 1.86–1.99(m, 4H), 2.47(t, 4H, J=7.0 Hz), 2.50(br, 8H), 2.73(t, 4H, J=7.0 Hz), 3.60(s, 6.H), 3.86(s, 6H), 3.92(s, 6H), 4.08(s, 6H), 6.28(s, 2H), 6.50(s, 2H).

m/z (EI): 608 [M$^+$].

EXAMPLE 26

Synthesis of N,N'-bis[3-(1-methyl-4,5,6-trimethoxy-indol-2-yl)propyl]homopiperazine

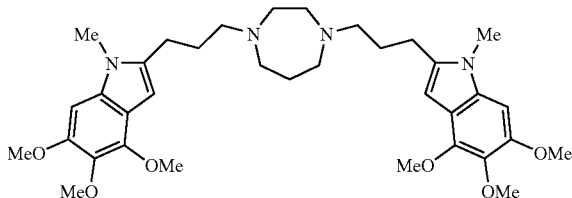

2-(3-Methanesulfonyloxypropyl)-1-methyl-4,5,6-tri-methoxyindole (130 mg) and homopiperazine (18 mg) were reacted in the same manner as in Example 1 to obtain the title compound as a free base.

Yield: 43 mg (38%).

$^1$H-NMR (400 MHz, CDCl$_3$) δ: 1.82–1.98(m, 6H), 2.64(t, 4H, J=7.0 Hz), 2.73(t, 4H, J=7.0 Hz), 2.78(br, 8H), 3.60(s, 6H), 3.86(s, 6H), 3.92(s, 6H), 4.08(s, 6H), 6.27(s, 2H), 6.50(s, 2H).

m/z (EI): 622 [M$^+$].

PREPARATION EXAMPLE 57

Synthesis of Methyl 2-nitro-3,4,5-trimethoxybenzoate

Methyl 3,4,5-trimethoxybenzoate (13.0 g) was dissolved in acetic anhydride (60 mL), a 1:20 mixed liquid (9 mL) of fuming nitric acid and concentrated nitric acid was slowly added dropwise at −10° C. to the solution, and the resultant mixture was stirred for 3 hours under ice cooling. Acetic anhydride was distilled off, water and an aqueous solution of potassium carbonate were added to the residue, and the mixture was stirred at room temperature for 40 minutes and then extracted with ethyl acetate. The resultant organic layer was washed with water and saturated brine, dried over anhydrous magnesium sulfate and then concentrated under reduced pressure. The residue was purified by column chromatography on silica gel (ethyl acetate:hexane=1:2) to obtain the title compound.

Yield: 7.34 g (47%).

$^1$H-NMR (400 MHz, CDCl$_3$) δ: 3.88(s, 3H), 3.95(s, 3H), 3.96(s, 3H), 3.97(s, 3H), 7.28(s, 1H).

PREPARATION EXAMPLE 58

Synthesis of 2-nitro-3,4,5-trimethoxybenzoic acid

Methyl 2-nitro-3,4,5-trimethoxybenzoate (6.9 g) was treated in the same manner as in Preparation Example 2 to obtain the title compound.

Yield: 5.9 g (90%).

$^1$H-NMR (400 MHz, CDCl$_3$) δ: 3.96(s, 3H), 4.00(s, 3H), 3.97(s, 3H), 7.35(s, 1H).

PREPARATION EXAMPLE 59

Synthesis of N-ethoxycarbonyl-2-nitro-3,4,5-trimethoxyaniline

2-Nitro-3,4,5-trimethoxybenzoic acid (4.7 g) was dissolved in dry benzene (70 mL), triethylamine (2.56 mL) and diphenylphosphoryl azide (4.15 mL) were added to the solution, and the mixture was stirred for 2 hours under reflux. Dry ethanol (140 mL) was added to the reaction mixture, and the mixture was further stirred overnight under reflux. After the reaction mixture was concentrated under reduced pressure, the residue was extracted with ethyl acetate. The resultant organic layer was washed with diluted hydrochloric acid, an aqueous solution of potassium carbonate, water and saturated brine, dried over anhydrous magnesium sulfate and then concentrated under reduced pressure. The residue was purified by column chromatography on silica gel (ethyl acetate:hexane=1:4 to 1:3) to obtain the title compound.

Yield: 2.8 g (54%).

$^1$H-NMR (400 MHz, CDCl$_3$) δ: 1.44(t, 3H, J=7.1 Hz), 3.88(s, 3H), 3.95(s, 3H), 4.03(s, 3H), 4.44(q, 2H, J=7.1 Hz), 7.94(s, 1H).

PREPARATION EXAMPLE 60

Synthesis of 2-nitro-3,4,5-trimethoxyaniline

N-Ethoxycarbonyl-2-nitro-3,4,5-trimethoxyaniline (2.8 g) was treated in the same manner as in Preparation Example 49 to obtain the title compound.

Yield: 2.05 g (92%).

$^1$H-NMR (400 MHz, CDCl$_3$) δ: 3.79(s, 3H), 3.87(s, 3H), 3.99(s, 3H), 5.28(br, 2H), 5.97(s, 1H).

PREPARATION EXAMPLE 61

Synthesis of 1,2-diamino-3,4,5-trimethoxybenzene

2-Nitro-3,4,5-trimethoxyaniline (913 mg) was treated in the same manner as in Preparation Example 18 to obtain the title compound.

Yield: 675 mg (85%).

$^1$H-NMR (400 MHz, CDCl$_3$) δ: 3.78(s, 3H), 3.81(s, 3H), 3.90(s, 3H), 6.13(s, 1H).

PREPARATION EXAMPLE 62

Synthesis of 1,2-di(benzyloxyacetamido)-3,4,5-trimethoxybenzene 1,2-Diamino-3,4,5-trimethoxybenzene (675 mg) and triethylamine (1.4 mL) were dissolved in dry dichloromethane (25 mL), benzyloxyacetyl chloride (1.34 mL) was added to the solution under ice cooling, and the mixture was stirred for 4 hours as it is. The reaction mixture was extracted with chloroform, and the resultant organic layer was washed with diluted hydrochloric acid, an aqueous solution of potassium carbonate, water and saturated brine, dried over anhydrous magnesium sulfate and then concentrated under reduced pressure. The residue was purified by column chromatography on silica gel (ethyl acetate:hexane=2:3 to 1:1) to obtain the title compound.

Yield: 1.4 g (85%).

$^1$H-NMR (400 MHz, CDCl$_3$) δ: 2.85(s, 3H), 3.86(s, 3H), 3.87(s, 3H), 3.99(s, 2H), 4.10(s, 2H), 4.61(s, 4H), 7.28–7.42 (m, 10H), 8.38(br, 1H), 9.36(br, 1H).

PREPARATION EXAMPLE 63

Synthesis of 2-hydroxymethyl-4,5,6-trimethoxy-benzimidazole 1,2-Di(benzyloxyacetamido)-3,4,5-trimethoxybenzene (1.9 g) was dissolved in xylene (30 mL), p-toluenesulfonic acid monohydrate (2.0 g) was added to the solution, and the mixture was stirred for 3 hours under reflux. After cooling, methanol saturated with ammonia was added to the reaction mixture into a uniform solution. The solution was concentrated under reduced pressure, and the residue was purified by column chromatography on silica gel (chloroform:methanol=15:1 to 10:1) to obtain the title compound.

Yield: 425 mg (46%).

$^1$H-NMR (400 MHz, CDCl$_3$) δ: 3.63(s, 3H), 3.79(s, 3H), 4.17(br, 3H), 4.56–4.64(m, 2H), 5.56(br, 1H), 6.69(br, 1H), 12.11(br, 1H).

PREPARATION EXAMPLE 64

Synthesis of 2-chloromethyl-4,5,6-trimethoxy-benzimidazole

2-Hydroxymethyl-4,5,6-trimethoxybenzimidazole (398 mg) was treated in the same manner as in Preparation Example 4 to obtain the title compound.

Yield: 465 mg (95%).

$^1$H-NMR (400 MHz, CDCl$_3$) δ: 3.91(s, 3H), 3.94(s, 3H), 4.17(s, 3H), 5.16(s, 2H), 7.00(s, 1H).

EXAMPLE 27

Synthesis of N,N'-bis[(4,5,6-trimethoxybenzimidazol-2-yl)methyl]piperazine

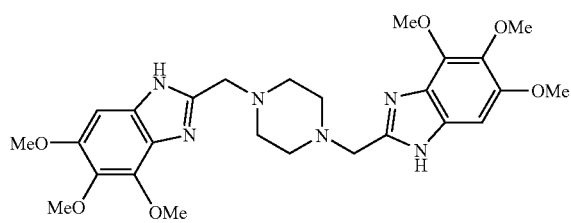

2-Chloromethyl-4,5,6-trimethoxybenzimidazole (250 mg) and piperazine (34 mg) were reacted in the same manner as in Example 1 to obtain the title compound as a free base.

Yield: 183 mg (87%).

$^1$H-NMR (400 MHz, CDCl$_3$) δ: 2.61(br, 8H), 3.80(s, 4H), 3.83(br, 3H), 4.09(br, 3H), 4.30(br, 3H), 6.65(br, 1H), 6.96 (br, 1H), 9.41(br, 2H).

m/z (EI): 540[M$^+$].

EXAMPLE 28

Synthesis of N,N'-bis[(4,5,6-trimethoxybenzimidazol-2-yl)methyl]homopiperazine

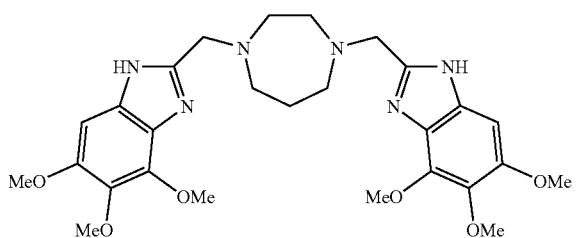

2-Chloromethyl-4,5,6-trimethoxybenzimidazole (200 mg) and homopiperazine (30 mg) were reacted in the same manner as in Example 1 to obtain the title compound as a free base.

Yield: 100 mg (62%).

m/z (EI): 540 [M1$^+$].

PREPARATION EXAMPLE 65

Synthesis of 2-tert-butyldimethylsilyloxymethyl-4,5,6-trimethoxybenzimidazole

2-Hydroxymethyl-4,5,6-trimethoxybenzimidazole (354 mg) was dissolved in dry DMF (2 mL), tert-butyldimethylchlorosilane (270 mg) and imidazole (45 mg) were added to the solution under ice cooling, and the mixture was stirred at room temperature for 30 minutes. Water was added to the reaction mixture to conduct extraction with ethyl acetate. The resultant organic layer was washed with water and saturated brine, dried over anhydrous magnesium sulfate and then concentrated under reduced pressure. The residue was purified by preparative TLC on silica gel (chloroform:methanol=12:1) to obtain the title compound.

Yield: 517 mg (99%).

$^1$H-NMR (400 MHz, CDCl$_3$) δ: 0.05(s, 6H), 0.86(s, 9H), 3.74(s, 3H), 3.74(s, 3H), 4.06(br, 3H), 4.80(s, 2H), 6.64(br, 1H).

PREPARATION EXAMPLE 66

Synthesis of Mixture of 2-tert-butyldimethylsilyloxymethyl-1-methyl-4,5,6-trimethoxy-benzimidazole and 2-tert-butyldimethylsilyloxymethyl-1-methyl-5,6,7-trimethoxybenzimidazole 2-tert-Butyldimethylsilyloxymethyl-4,5,6-trimethoxybenzimidazole (517 mg) was dissolved in dry DMF, sodium hydride (87 mg) and iodomethane (0.28 mL) were added to the solution, and the mixture was stirred at room temperature for 1 hour. Water was added to the reaction mixture to conduct extraction with ethyl acetate. The resultant organic layer was washed with water and saturated brine, dried over anhydrous magnesium sulfate and then concentrated under reduced pressure. The residue was purified by preparative TLC on silica gel (chloroform:methanol=12:1) to obtain a mixture of the title compounds.

Yield: 471 mg (87%).

PREPARATION EXAMPLE 67

Synthesis of 2-hydroxymethyl-1-methyl-4,5,6-trimethoxybenzimidazole

A mixture (471 mg) of 2-tert-butyldimethylsilyloxymethyl-1-methyl-4,5,6-trimethoxybenzimidazole and 2-tert-butyldimethylsilyloxymethyl-1-methyl-5,6,7-trimethoxybenzimidazole was dissolved in a mixed solvent of acetic acid (5 mL), water (2.5 mL) and THF (2.5 mL), and the solution was stirred at 90° C. for 2 hours. Saturated brine was added to the reaction mixture, and the mixture was alkalified with an aqueous solution of potassium carbonate and then extracted with ethyl acetate. The resultant organic layer was washed with saturated brine, dried over anhydrous magnesium sulfate and then concentrated under reduced pressure. The residue was purified by preparative TLC on silica gel (chloroform:methanol=13:1) to obtain a mixture of the title compounds.

yield: 130 mg (40%).
$^1$H-NMR (400 MHz, CDCl$_3$) δ: 3.73(s, 3H), 3.87(s, 3H), 3.90(s, 3H), 4.27(s, 3H), 4.86(s, 2H), 6.36(s, 1H).

PREPARATION EXAMPLE 68

Synthesis of 2-hydroxymethyl-1-methyl-5,6,7-trimethoxybenzimidazole

The title compound of an isomer was isolated by the preparative TLC on silica gel described in Preparation Example 67.

Yield: 79 mg (24%).
$^1$H-NMR (400 MHz, CDCl$_3$) δ: 3.88(s, 3H), 3.89(s, 3H), 3.99(s, 3H), 4.00(s, 3H), 4.81(s, 2H), 6.92(s, 1H).

PREPARATION EXAMPLE 69

Synthesis of 2-chloromethyl-1-methyl-5,6,7-trimethoxybenzimidazole

2-Hydroxymethyl-1-methyl-5,6,7-trimethoxy-benzimidazole (79 mg) was treated in the same manner as in Preparation Example 4 to obtain the title compound.

Yield: 37 mg (45%).
$^1$H-NMR (400 MHz, CDCl$_3$) δ: 3.90(s, 3H), 3.91(s, 3H), 4.04(s, 3H), 4.05(s, 3H), 4.78(s, 2H), 6.97(s, 1H).

EXAMPLE 29

Synthesis of N,N'-bis[(1-methyl-5,6,7-trimethoxy-benzimidazol-2-yl)methyl]homopiperazine

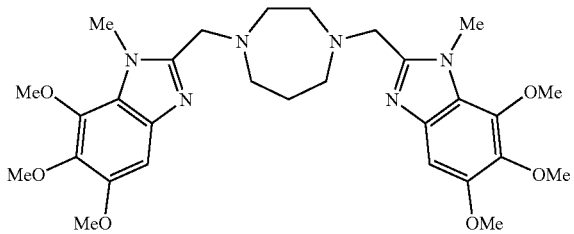

2-Chloromethyl-1-methyl-5,6,7-trimethoxy-benzimidazole (39 mg) and homopiperazine (7 mg) were reacted in the same manner as in Example 1 to obtain the title compound as a free base.

Yield: 30 mg (75%).
$^1$H-NMR (400 MHz, CDCl$_3$) δ: 1.81(quint, 2H, J=5.9 Hz), 2.69(s, 4H), 2.76(t, 4H, J=5.9 Hz), 3.82(s, 6H), 3.88(s, 4H), 3.90(s, 6H), 4.04(s, 12H), 6.95(s, 2H).
m/z (EI): 568 [M$^+$].

PREPARATION EXAMPLE 70

Synthesis of 2-chloromethyl-1-methyl-4,5,6-trimethoxybenzimidazole

2-Hydroxymethyl-1-methyl-4,5,6-trimethoxy-benzimidazole (131 mg) was treated in the same manner as in Preparation Example 4 to obtain the title compound.

Yield: 155 mg (97%).
$^1$H-NMR (400 MHz, CDCl$_3$) δ: 3.92(s, 3H), 4.00(s, 3H), 4.02(s, 3H), 4.19(s, 3H), 5.23(s, 2H), 6.80(s, 1H).

EXAMPLE 30

Synthesis of N,N'-bis[(1-methyl-4,5,6-trimethoxy-benzimidazol-2-yl)methyl]piperazine

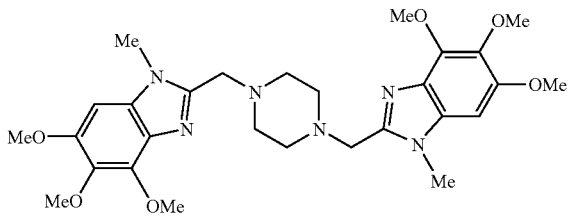

2-Chloromethyl-1-methyl-4,5,6-trimethoxy-benzimidazole (75 mg) and piperazine (10 mg) were reacted in the same manner as in Example 1 to obtain the title compound as a free base.

Yield: 44 mg (73%).
$^1$H-NMR (400 MHz, CDCl$_3$) δ: 2.50(s, 8H), 3.76(s, 4H), 3.79(s, 6H), 3.87(s, 6H), 3.93(s, 6H), 4.27(s, 6H), 6.50(s, 2H).
m/z (EI): 544 [M$^+$].

EXAMPLE 31

Synthesis of N,N'-bis[(1-methyl-4,5,6-trimethoxy-benzimidazol-2-yl)methyl]homopiperazine

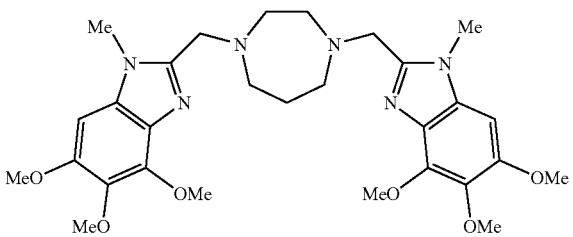

2-Chloromethyl-1-methyl-4,5,6-trimethoxy-benzimidazole (75 mg) and homopiperazine (11 mg) were reacted in the same manner as in Example 1 to obtain the title compound as a free base.

Yield: 67 mg (theoretical amount).
$^1$H-NMR (400 MHz, CDCl$_3$) δ: 1.78(quint, 2H, J=5.6 Hz), 2.66(s, 4H), 2.75(t, 4H, J=5.6 Hz), 3.81(s, 6H), 3.86(s, 4H), 3.86(s, 6H), 3.93(s, 6H), 4.29(s, 6H), 6.50(s, 2H).
m/z (EI): 568 [M$^+$].

PREPARATION EXAMPLE 71

Synthesis of Ethyl 3,4,5-trimethoxyoxanilate 3,4,5-Trimethoxyaniline (3.0 g) and triethylamine (4.5 mL) were dissolved in dichloromethane (10 mL), ethyl chloroglyoxylate (1.89 mL) was added dropwise to the solution under ice cooling, and the mixture was stirred for 2 hours. 1 M Hydrochloric acid was added to the reaction mixture to conduct extraction with dichloromethane. The resultant organic layer was washed with water and saturated brine, dried over anhydrous magnesium sulfate and then concentrated under reduced pressure to obtain the title compound.
Yield: 4.53 g (97%).
$^1$H-NMR (400 MHz, CDCl$_3$) δ: 1.41(t, 3H, J=7.2 Hz), 3.80(s, 3H), 3.84(s, 6H), 4.39(q, 2H, J=7.2 Hz), 6.93(s, 2H).

PREPARATION EXAMPLE 72

Synthesis of Ethyl (3,4,5-trimethoxyphenylamino)-thioxoacetate

Ethyl 3,4,5-trimethoxyoxanilate (3.0 g) was dissolved in benzene (20 mL), and 2,4-bis(4-methoxyphenyl)-1,3-dithia-2,4-diphosphetane-2,4-disulfide (2.14 g) was added to the solution. The reaction mixture was stirred at 80° C. for 1 hour, and water was added thereto. After conducting extraction with ethyl acetate, the resultant organic layer was washed with water and saturated brine, dried over anhydrous magnesium sulfate and then concentrated under reduced pressure. The residue was purified by column chromatography on silica gel (ethyl acetate:hexane=1:4) to obtain the title compound.
Yield: 2.30 g (72%).
$^1$H-NMR (400 MHz, CDCl$_3$) δ: 1.43(t, 3H, J=7.2 Hz), 3.84(s, 3H), 3.85(s, 6H), 4.42(q, 2H, J=7.2 Hz), 7.38(s, 2H).

PREPARATION EXAMPLE 73

Synthesis of 2-ethoxycarbonyl-5,6,7-trimethoxy-benzothiazole

Ethyl (3,4,5-trimethoxyphenylamino)thioxyacetate (2.04 g) was dissolved in chloroform (10 mL), and bromine (0.3 mL) was added dropwise to the solution at −20° C. After the mixture was stirred for 1 hour as it is, it was stirred further for 3 hours at room temperature. Water was added to the reaction mixture to conduct extraction with dichloromethane, and the resultant organic layer was washed with water and saturated brine, dried over anhydrous magnesium sulfate and then concentrated under reduced pressure. The residue was purified by column chromatography on silica gel (ethyl acetate:hexane=1:9) to obtain the title compound.
Yield: 1.39 g (69%).
$^1$H-NMR (400 MHz, CDCl$_3$) δ: 1.48(t, 3H, J=7.1 Hz), 3.95(s, 3H), 3.96(s, 3H), 4.10(s, 3H), 4.53(q, 2H, J=7.1 Hz), 7.47(s, 1H).

PREPARATION EXAMPLE 74

Synthesis of 2-hydroxymethyl-5,6,7-trimethoxy-benzothiazole

2-Ethoxycarbonyl-5,6,7-trimethoxybenzothiazole (1.04 g) was dissolved in methanol (30 mL), sodium borohydride (331 mg) was added to the solution under ice cooling, and the mixture was stirred at room temperature for 2 hours. Sodium borohydride (100 mg) was additionally added to the reaction mixture to conduct stirring for 2 hours. The reaction mixture was concentrated under reduced pressure, and the residue was purified by column chromatography on silica gel (ethyl acetate:hexane=1:1) to obtain the title compound.
Yield: 854 mg (95%).
$^1$H-NMR (400 MHz, CDCl$_3$) δ: 3.90(s, 3H), 3.91(s, 3H), 4.05(s, 3H), 5.01(s, 2H), 7.19(s, 1H).

PREPARATION EXAMPLE 75

Synthesis of 2-chloromethyl-5,6,7-trimethoxy-benzothiazole

2-Hydroxymethyl-5,6,7-trimethoxybenzothiazole (620 mg) was treated in the same manner as in Preparation Example 4 to obtain the title compound.
Yield: 563 mg (85%).
$^1$H-NMR (400 MHz, CDCl$_3$) δ: 3.85(s, 3H), 3.87(s, 3H), 4.00(s, 3H), 4.82(s, 2H), 7.20(s, 1H).

EXAMPLE 32

Synthesis of N,N'-bis[(5,6,7-trimethoxybenzothiazol-2-yl)methyl]piperazine

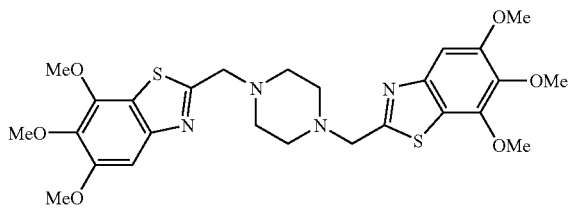

2-Chloromethyl-5,6,7-trimethoxybenzothiazole (365 mg) and piperazine (58 mg) were reacted in the same manner as in Example 1 to obtain the title compound as a free base.
Yield: 123 mg (33%).
$^1$H-NMR (400 MHz, CDCl$_3$) δ: 2.74(br, 8H), 3.92(s, 6H), 3.93(s, 6H), 4.07(s, 6H), 7.25(s, 2H).
m/z (EI): 560 [M$^+$].

EXAMPLE 33

Synthesis of N,N'-bis[(5,6,7-trimethoxybenzothiazol-2-yl)methyl]homopiperazine

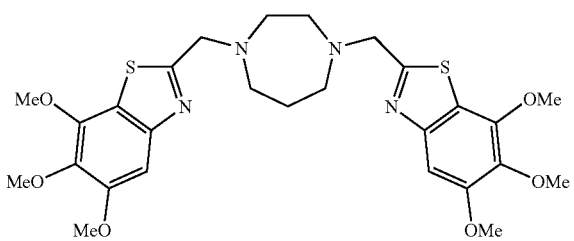

2-Chloromethyl-5,6,7-trimethoxybenzothiazole (200 mg) and homopiperazine (37 mg) were reacted in the same manner as in Example 1 to obtain the title compound as a free base.

Yield: 89 mg (42%).

$^1$H-NMR (400 MHz, CDCl$_3$) δ: 1.91–1.94(m, 2H), 2.93–2.97(m, 8H), 3.92(s, 6H), 3.93(s, 6H), 4.08(s, 4H), 4.09(s, 6H), 7.24(s, 2H).

m/z (EI): 574 [M$^+$].

PREPARATION EXAMPLE 76

Synthesis of 5,6,7-trimethoxybenzothiazole-2-carboaldehyde

Oxalyl chloride (0.78 mL) was dissolved in dichloromethane (10 mL), DMSO (1.49 mL) was added dropwise at −78° C., and the mixture was stirred for 30 minutes. After a solution of 2-hydroxymethyl-5,6,7-trimethoxy-benzothiazole (1.53 g) in dichloromethane (10 mL) was added dropwise at −78° C. to the mixture, stirring was conducted for 1 hour, triethylamine (6.46 mL) was added, and the resultant mixture was warmed to room temperature. After an aqueous solution of ammonium chloride was added to the mixture, extraction was conducted with dichloromethane. The resultant organic layer was washed with saturated brine, dried over anhydrous magnesium sulfate and then concentrated under reduced pressure. The residue was purified by column chromatography on silica gel (ethyl acetate:hexane=1:9) to obtain the title compound.

Yield: 1.46 g (96%).

$^1$H-NMR (400 MHz, CDCl$_3$) δ: 3.98(s, 3H), 3.99(s, 3H), 4.10(s, 3H), 7.44(s, 1H), 10.08(s, 1H).

PREPARATION EXAMPLE 77

Synthesis of Ethyl 3-(5,6,7-trimethoxybenzothiazol-2-yl)propenoate 5,6,7-Trimethoxybenzothiazole-2-carboaldehyde (951 mg) was treated in the same manner as in Preparation Example 17 to obtain the title compound.

Yield: 908 mg (75%).

$^1$H-NMR (400 MHz, CDCl$_3$) δ: 1.36(t, 3H, J=7.1 Hz), 3.94(s, 3H), 3.96(s, 3H), 4.08(s, 3H), 4.30(q, 2H, J=7.1 Hz), 6.76(d, 1H, J=15.8 Hz), 7.32(s, 1H), 7.81(d, 1H, J=15.9 Hz).

PREPARATION EXAMPLE 78

Synthesis of Ethyl 3-(5,6,7-trimethoxybenzothiazol-2-yl)propionate

Ethyl 3-(5,6,7-trimethoxybenzothiazol-2-yl)-propenoate (908 mg) was treated in the same manner as in Preparation Example 18 to obtain the title compound.

Yield: 660 mg (72%).

PREPARATION EXAMPLE 79

Synthesis of 2-(3-hydroxypropyl)-5,6,7-trimethoxy-benzothiazole

Ethyl 3-(5,6,7-trimethoxybenzothiazol-2-yl)propionate (660 mg) was treated in the same manner as in Preparation Example 19 to obtain the title compound.

Yield: 420 mg (73%).

$^1$H-NMR (400 MHz, CDCl$_3$) δ: 2.01–2.07(m, 2H), 3.13(t, 2H, J=7.2 Hz), 3.71(t, 2H, J=5.8 Hz), 3.83(s, 3H), 3.85(s, 3H), 3.98(s, 3H), 7.16(s, 1H).

PREPARATION EXAMPLE 80

Synthesis of 2-(3-bromopropyl)-5,6,7-trimethoxy-benzothiazole 2-(3-Hydroxypropyl)-5,6,7-trimethoxybenzothiazole (388 mg) was dissolved in dichloromethane (5 mL), carbon tetrabromide (590 mg) and triphenylphosphine (431 mg) were added to the solution at room temperature, and the mixture was vigorously stirred for 1 hour. Water was added to conduct extraction with dichloromethane, and the resultant organic layer was washed with saturated brine, dried over anhydrous magnesium sulfate and then concentrated under reduced pressure. The residue was purified by column chromatography on silica gel (ethyl acetate:hexane=1:9) to obtain the title compound.

Yield: 328 mg (66%).

$^1$H-NMR (400 MHz, CDCl$_3$) δ: 2.32–2.38(m, 2H), 3.16(t, 2H, J=7.2 Hz), 3.45(t, 2H, J=6.5 Hz), 3.84(s, 3H), 3.85(s, 3H), 3.98(s, 3H), 7.18(s, 1H).

EXAMPLE 34

Synthesis of N,N'-bis[3-(5,6,7-trimethoxybenzothiazol-2-yl)propyl]piperazine

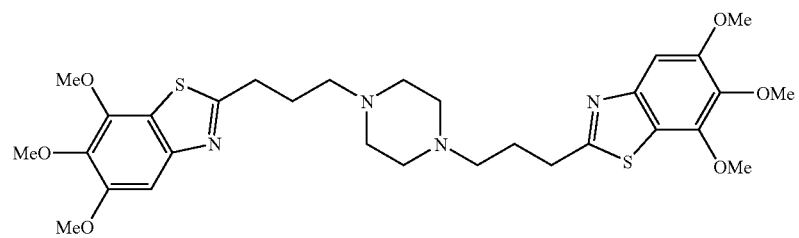

2-(3-Bromopropyl)-5,6,7-trimethoxybenzothiazole (328 mg) and piperazine (39 mg) were reacted in the same manner as in Example 1 to obtain the title compound as a free base.

Yield: 61 mg (23%).

$^1$H-NMR (400 MHz, CDCl$_3$) δ: 2.03–2.07(m, 4H), 2.45–2.48(m, 12H), 3.10(t, 4H, J=7.6 Hz), 3.91(s, 6H), 3.93(s, 6H), 4.06(s, 6H), 7.25(s, 2H).

m/z (EI): 616[M$^+$].

EXAMPLE 35

Synthesis of N,N'-bis[3-(5,6,7-trimethoxybenzothiazol-2-yl)propyl]homopiperazine

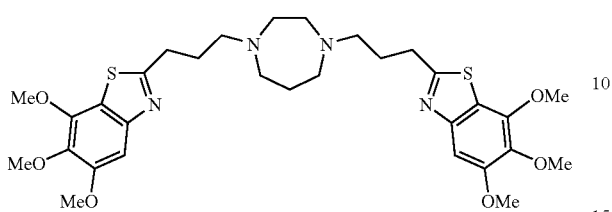

2-(3-Bromopropyl)-5,6,7-trimethoxybenzothiazole (444 mg) and homopiperazine (64 mg) were reacted in the same manner as in Example 1 to obtain the title compound as a free base.

Yield: 84 mg (21%).

$^1$H-NMR (400 MHz, CDCl$_3$) δ: 1.82–1.93(m, 2H), 2.00–2.12(m, 4H), 2.64(t, 4H, J=7.2 Hz), 2.75–2.77(m, 8H), 3.10(t, 4H, J=7.4 Hz), 3.91(s, 6H), 3.93(s, 6H), 4.06(s, 6H), 7.25(s, 2H).

m/z (EI): 630 [M$^+$].

PREPARATION EXAMPLE 81

Synthesis of (6'-nitro-2',3',4'-trimethoxyphenyl)benzyloxyacetate

6-Nitro-2,3,4-trimethoxyphenol (1.25 g) and triethylamine (1.12 mL) were dissolved in dichloromethane (20 mL), benzyloxyacetyl chloride (1.1 mL) was added dropwise to the solution under ice cooling, and the mixture was stirred for 2 hours as it is. The reaction mixture was extracted with chloroform, and the extract was washed with water and saturated brine, dried over anhydrous magnesium sulfate and then concentrated under reduced pressure. The residue was purified by column chromatography on silica gel (ethyl acetate:hexane=1:4) to obtain the title compound.

Yield: 1.38 g (66.5%).

PREPARATION EXAMPLE 82

Synthesis of 2-hydroxymethyl-5,6,7-trimethoxy-benzoxazole (6'-Nitro-2',3',4'-trimethoxyphenyl)benzyloxyacetate (1.38 g) was dissolved in methanol (40 mL), 10% palladium on carbon was added to the solution, and the mixture was stirred at room temperature for 7 hours under a hydrogen atmosphere. The reaction mixture was filtered, and the filtrate was concentrated. The residue was dissolved in xylene (50 mL), p-toluenesulfonic acid monohydrate (350 mg) was added to the solution, and the mixture was stirred for 1 hour under reflux. After the reaction mixture was concentrated under reduced pressure, water was added to the residue to conduct extraction with ethyl acetate. The extract was washed with water and saturated brine, dried over anhydrous magnesium sulfate and then concentrated under reduced pressure. The residue was purified by preparative TLC on silica gel (chloroform:methanol=10:1) to obtain the title compound.

Yield: 126 mg (12%).

PREPARATION EXAMPLE 83

Synthesis of 2-chloromethyl-5,6,7-trimethoxy-benzoxazole

2-Hydroxymethyl-5,6,7-trimethoxybenzoxazole (114 mg) was treated in the same manner as in Preparation Example 4 to obtain the title compound.

Yield: 95 mg (83%).

EXAMPLE 36

Synthesis of N,N'-bis[(5,6,7-trimethoxybenzoxazol-2-yl)methyl]piperazine

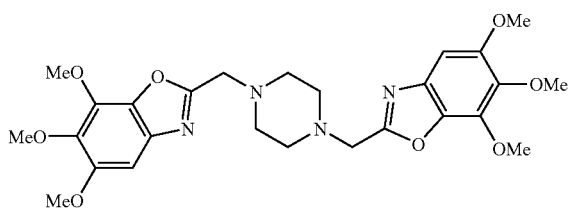

2-Chloromethyl-5,6,7-trimethoxybenzoxazole (156 mg) and piperazine (23 mg) were reacted in the same manner as in Example 1 to obtain the title compound as a free base.

Yield: 135 mg (95%).

$^1$H-NMR (400 MHz, CDCl$_3$) δ: 2.74(br, 8H), 3.86(s, 4H), 3.89(s, 6H), 3.89(s, 6H), 4.20(s, 6H), 6.89(s, 2H). m/z: 528 [M$^+$].

EXAMPLE 37

Synthesis of N,N'-bis[(5,6,7-trimethoxybenzoxazol-2-yl)methyl]homopiperazine

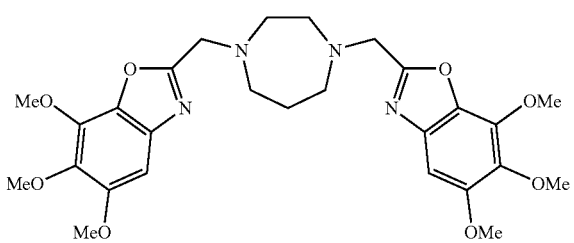

2-Chloromethyl-5,6,7-trimethoxybenzoxazole (152 mg) and homopiperazine (28 mg) were reacted in the same manner as in Example 1 to obtain the title compound as a free base.

Yield: 121 mg (81%).

$^1$H-NMR (400 MHz, CDCl$_3$) δ: 1.87(quint, 2H), 2.85–2.97(m, 8H), 3.89(s, 6H), 3.89(s, 6H), 4.00(s, 4H), 4.20(s, 6H), 6.90(s, 2H). m/z: 542 [M$^+$].

PREPARATION EXAMPLE 84

Synthesis of Ethyl 2-(3,4,5-trimethoxyphenyloxy)-acetoacetate 3,4,5-Trimethoxyphenol (5.83 g) was dissolved in DMF (60 mL), and potassium tert-butoxide (3.55 g) was added to the solution under ice cooling. Ethyl 2-chloroacetoacetate (4.46 mL) was then added, and the mixture was stirred at room temperature for 3 hours. The reaction mixture was heated to 80° C. and stirred for 2 hours. After allowing the reaction mixture to cool, water was added to the reaction mixture to conduct extraction with ethyl acetate. The resultant organic layer was washed with water and saturated brine, dried over anhydrous magnesium sulfate and then concentrated under reduced pressure. The residue was purified by column chromatography on silica gel (ethyl acetate:hexane=1:3) to obtain the title compound.

Yield: 5.3 g (54%).

PREPARATION EXAMPLE 85

Synthesis of Ethyl 3-methyl-4,5,6-trimethoxbenzofuran-2-carboxylate

Ethyl 2-(3,4,5-trimethoxyphenyloxy)acetoacetate (5.3 g) was slowly added dropwise to concentrated hydrochloric acid (10 mL) under ice cooling, and the mixture was stirred for 1 hour as it is. Water was added to the reaction mixture to conduct extraction with ethyl acetate. The extract was washed with water and saturated brine, dried over anhydrous magnesium sulfate and then concentrated under reduced pressure. The residue was recrystallized from ethyl acetate and hexane to obtain the title compound.

Yield: 3.2 g (64%).

PREPARATION EXAMPLE 86

Synthesis of 3-methyl-4,5,6-trimethoxbenzofuran-2-carboxylic acid

Ethyl 3-methyl-4,5,6-trimethoxbenzofuran-2-carboxylate was treated in the same manner as in Preparation Example 2 to obtain the title compound.

Yield: 411 mg (91%).

PREPARATION EXAMPLE 87

Synthesis of N,N'-bis(3-methyl-4,5,6-trimethoxy-benzofuran-2-carbonyl)piperazine 3-Methyl-4,5,6-trimethoxbenzofuran-2-carboxylic acid (300 mg) and piperazine (49 mg) were reacted in the same manner as in Preparation Example 37 to obtain the title compound.

Yield: 151 mg (47%).

EXAMPLE 38

Synthesis of N,N'-bis[(3-methyl-4,5,6-trimethoxy-benzofuran-2-yl)methyl]piperazine

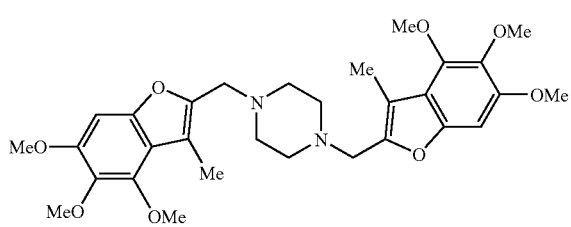

N,N'-Bis(3-methyl-4,5,6-trimethoxybenzofuran-2-carbonyl)piperazine (93 mg) was treated in the same manner as in Example 18: to obtain the title compound as a free base.

Yield: 65 mg (74%). m/z: 554 [M+].

PREPARATION EXAMPLE 88

Synthesis of N,N'-bis(3-methyl-4,5,6-trimethoxy-benzofuran-2-carbonyl)homopiperazine 3-Methyl-4,5,6-trimethoxbenzofuran-2-carboxylic acid (117 mg) and homopiperazine (20 mg) were reacted in the same manner as in Preparation Example 37 to obtain the title compound.

Yield: 117 mg (98%).

EXAMPLE 39

Synthesis of N,N'-bis[(3-methyl-4,5,6-trimethoxy-benzofuran-2-yl)methyl]homopiperazine

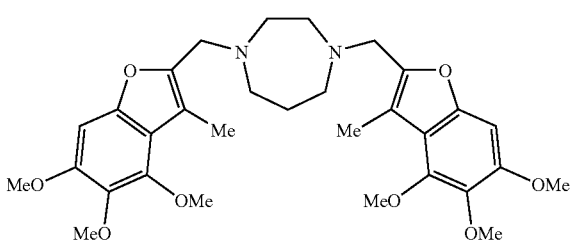

N,N'-Bis(3-methyl-4,5,6-trimethoxybenzofuran-2-carbonyl)homopiperazine (117 mg) was treated in the same manner as in Example 18 to obtain the title compound as a free base.

Yield: 82 mg (72%).

$^1$H-NMR (400 MHz, CDCl$_3$) δ: 1.78–1.87(m, 2H), 2.29(s, 3H), 2.75–2.82(m, 8H), 3.70(s, 4H), 3.86(s, 6H), 3.87(s, 6H), 3.98(s, 6H), 6.76(s, 2H). m/z: 568 [M+].

PREPARATION EXAMPLE 89

Synthesis of Ethyl 4,5,6-trimethoxbenzothiophene-2-carboxylate

6-Nitro-2,3,4-trimethoxybenzaldehyde (1.6 g) was dissolved in DMF (15 mL), and potassium carbonate (1.28 g) was added to the solution. Methyl thioglycolate (0.68 mL) was added dropwise to the mixture under ice cooling, and stirring was conducted for 40 minutes. The mixture was then stirred at room temperature for 4 hours. Water was added to the reaction mixture to conduct extraction with ethyl acetate. The resultant organic layer was washed with saturated brine, dried over anhydrous magnesium sulfate and then concentrated under reduced pressure. The residue was purified by column chromatography on silica gel (ethyl acetate:hexane=1:4) to obtain the title compound.

Yield: 1.22 g (64%).

$^1$H-NMR (400 MHz, CDCl$_3$) δ: 3.91(s, 3H), 3.92(s, 3H), 3.95(s, 3H), 4.07(s, 3H), 7.04(s, 1H), 8.01(s, 1H).

PREPARATION EXAMPLE 90

Synthesis of 2-hydroxymethyl-4,5,6-trimethoxy-benzothiophene

Ethyl 4,5,6-trimethoxbenzothiophene-2-carboxylate (550 mg) was treated in the same manner as in Preparation Example 3 to obtain the title compound.

Yield: 602 mg (theoretical amount).

$^1$H-NMR (400 MHz, CDCl$_3$) δ: 1.90(br, 1H), 3.83(s, 3H), 3.84(s, 3H), 3.95(s, 3H), 4.80(d, 2H, J=5.1 Hz), 6.97(s, 1H), 7.17(s, 1H).

EXAMPLE 40

Synthesis of N,N'-bis[(4,5,6-trimethoxybenzothiophen-2-yl)methyl]piperazine

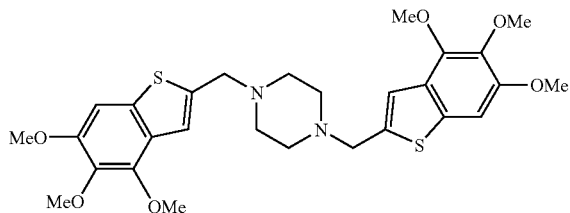

2-Hydroxymethyl-4,5,6-trimethoxbenzothiophene (374 mg) was treated in the same manner as in Preparation Example 4, and 2-chloromethyl-4,5,6-trimethoxy-benzothiophene thus obtained was immediately reacted with piperazine (63 mg) in the same manner as in Example 1 without isolating it to obtain the title compound as a free base.

Yield: 17 mg (2%).

$^1$H-NMR (400 MHz, CDCl$_3$) δ: 2.57(br, 8H), 3.75(s, 4H), 3.89(s, 6H), 3.90(s, 6H), 4.02(s, 6H), 7.02(s, 2H), 7.15(s, 2H).

m/z (EI): 558 [M$^+$].

EXAMPLE 41

Synthesis of N,N'-bis[(4,5,6-trimethoxybenzothiophen-2-yl)methyl]homopiperazine

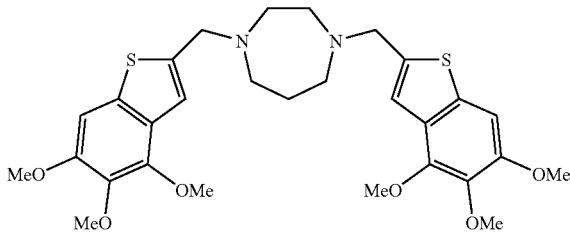

2-Hydroxymethyl-4,5,6-trimethoxbenzothiophene (1.15 g) was treated in the same manner as in Preparation Example 4, and 2-chloromethyl-4,5,6-trimethoxy-benzothiophene thus obtained was immediately reacted with homopiperazine (226 mg) in the same manner as in Example 1 without isolating it to obtain the title compound as a free base.

Yield: 242 mg (9%).

$^1$H-NMR (400 MHz, CDCl$_3$) δ: 1.81–1.83(m, 2H), 2.75–2.82(m, 8H), 3.88(s, 4H), 3.89(s, 6H), 3.90(s, 6H), 4.02(s, 6H), 7.03(s, 2H), 7.14(s, 2H).

m/z (EI): 572 [M$^+$].

TEST EXAMPLE

Inhibitory Effect on Cell Adhesion

This test was conducted by reference to the method of Ross et al. (J. Biol. Chem., 267, 8537–8543(1992). More specifically, after human umbilical venous endothelial cells (HUVEC) were cultured on a 48-well plate to confluent growth, IL-1β or TNFα was added thereto. After culturing for 5 hours, U937, which is a human monocytic/histocytic cell fluorescence-labeled with PKH2(product of Dainippon Pharmaceutical Co., Ltd.), was added in a proportion of 1×10$^6$ cells per well. After the plate was left at rest at room temperature for 1 hour, unadhered U937 was washed out and lysed in 1% Triton X-100 to measure a remaining fluorescence intensity (excitation wavelength: 480 nm; measuring wavelength: 530 nm). HUVEC and U937 were cultured in EGM-2 (product of Sanko Junyaku K. K.) and 10% FCS-containing RPMI1640, respectively. Each test agent was added to HUVEC upon the addition of IL-1β or TNFα and to U937 24 hours prior to the cell adhesion test. The inhibitory activity was calculated out according to the equation [100−(C−B)/(A−B)×100(%)], wherein A is the number of U937 cells adhered to HUVEC stimulated by IL-1β or TNFα when no test agent was added, B is the number of U937 cells adhered to HUVEC not stimulated by IL-1β or TNFα when no test agent was added, and C is the number of U937 cells adhered to HUVEC stimulated by IL-1β or TNFα when the test agent was added. The results are shown in Table 1. As control compounds, Test Compound 1 described in Japanese Patent Application Laid-Open No. 9–143075 and dilazep described in Japanese Patent Application Laid-Open No. 11–92382 were simultaneously evaluated.

TABLE 1

Inhibitory activity of each compound at 1 μM against cell adhesion

| | Percent inhibition (%) | |
|---|---|---|
| Example | Stimulation by TNFα | Stimulation by IL-1β |
| 6 | 69 | 57 |
| 32 | 52 | 54 |
| 33 | 79 | 64 |
| 41 | 27 | 52 |
| Test compound 1 | 5 | 10 |
| Dilazep | 12 | 0 |

Specific formulation examples will hereinafter be described.

PREPARATION EXAMPLE 91

Capsule Preparation

| | |
|---|---|
| N,N'-Bis[2-(5,6,7-trimethoxynaphthalen-2-yl)ethyl]homopiperazine | 30 mg |
| Microcrystalline cellulose | 30 mg |
| Lactose | 57 mg |
| Magnesium stearate | 3 mg |
| Total amount | 120 mg. |

The above ingredients were mixed in accordance with a method known per se in the art and then charged in capsules to obtain capsule preparations.

PREPARATION EXAMPLE 92

Tablet Preparation

| | |
|---|---|
| N,N'-Bis[2-(5,6,7-trimethoxynaphthalen-2-yl)-ethyl]homopiperazine | 30 mg |
| Starch | 44 mg |
| Starch (for glue) | 5.6 mg |
| Magnesium stearate | 0.4 mg |
| Calcium carboxymethyl cellulose | 20 mg |
| Total amount | 100 mg. |

The above ingredients were mixed in accordance with a method known per se in the art to obtain tablet preparations.

PREPARATION EXAMPLE 93

Injection Preparation

N,N'-Bis[2-(5,6,7-trimethoxynaphthalen-2-yl)-ethyl]homopiperazine (100 mg) and sodium chloride (900 mg) were dissolved in distilled water (about 80 mL) for injection, and distilled water for injection was added to the resultant solution to 100 mL in total. This diluted solution was sterilized by filtration and then subdivided and charged into 10 ampoules, and the ampoules were sealed to obtain injection preparations.

As described above, the compounds (1) according to the present invention have inhibitory effects on both cell adhesion and cell infiltration and are useful as medicines for prevention or treatment of allergy, asthma, rheumatism, arteriosclerosis, inflammatory, etc.

Obviously, numerous modifications of the above teachings are apparent to those skilled in the art. Therefore, within the scope of the appended claims the invention may be practiced otherwise than as specifically described herein.

The invention claimed is:

1. A cyclic diamine compound of formula (1):

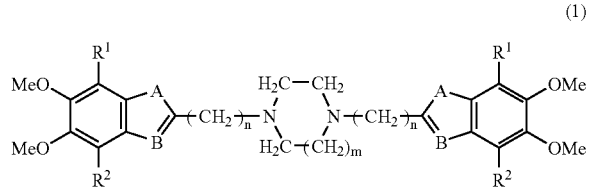

(1)

wherein $R^1$ and $R^2$ are individually a hydrogen atom or a methoxy group, provided $R^1$ is a methoxy group when $R^2$ is a hydrogen atom, or $R^1$ is a hydrogen atom when $R^2$ is a methoxy group; A is an oxygen atom, a sulfur atom, CH=CH, CH=N or $NR^3$, in which $R^3$ is a hydrogen atom, or a lower alkyl, hydroxy lower alkyl, lower alkoxy lower alkyl, aryl or aryl lower alkyl group; B is a nitrogen atom, CH or $CR^4$, in which $R^4$ is a hydrogen atom, or a lower alkyl, hydroxy lower alkyl, lower alkoxy lower alkyl, aryl or aryl lower alkyl group; m is 1 or 2; and n is a number of 1 to 5, an acid-addition salt thereof, or a hydrate thereof.

2. The cyclic diamine compound of claim 1, wherein $R^3$ and $R^4$ are individually a hydrogen atom, $C_1$–$C_6$-alkyl group, hydroxy-$C_2$–$C_6$-alkyl group, $C_1$–$C_6$-alkoxy-$C_1$–$C_6$-alkyl group, $C_6$–$C_{10}$-aryl or $C_6$–$C_{10}$-aryl-$C_1$–$C_6$-alkyl group.

3. The cyclic diamine compound of claim 2, wherein the ring system

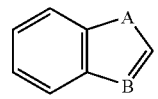

in formula (1) is selected from the group consisting of naphthalene, quinoline, quinazoline, benzimidazole, benzothiazole, benzoxazole, indole, benzothiophene and benzofuran.

4. A pharmaceutical composition comprising as an active ingredient a cyclic diamine compound of formula (1):

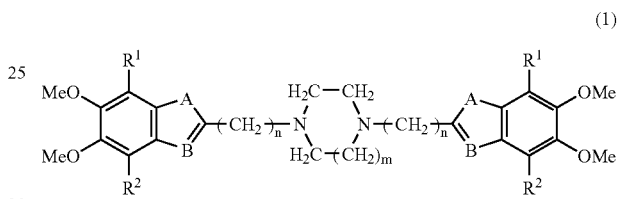

(1)

wherein $R^1$ and $R^2$ are individually a hydrogen atom or a methoxy group, provided $R^1$ is a methoxy group when $R^2$ is a hydrogen atom, or $R^1$ is a hydrogen atom when $R^2$ is a methoxy group; A is an oxygen atom, a sulfur atom, CH=CH, CH=N or $NR^3$, in which $R^3$ is a hydrogen atom, or a lower alkyl, hydroxy lower alkyl, lower alkoxy lower alkyl, aryl or aryl lower alkyl group; B is a nitrogen atom, CH or $CR^4$, in which $R^4$ is a hydrogen atom, or a lower alkyl, hydroxy lower alkyl, lower alkoxy lower alkyl, aryl or aryl lower alkyl group; m is 1 or 2; and n is a number of 1 to 5, an acid-addition salt thereof, or a hydrate thereof, and a pharmaceutically acceptable carrier.

5. The pharmaceutical composition of claim 4, wherein $R^3$ and $R^4$ are individually a hydrogen atom, $C_1$–$C_6$-alkyl group, hydroxy-$C_2$–$C_6$-alkyl group, $C_1$–$C_6$-alkoxy-$C_1$–$C_6$-alkyl group, $C_6$–$C_{10}$-aryl or $C_6$–$C_{10}$-aryl-$C_1$–$C_6$-alkyl group.

6. The pharmaceutical composition of claim 4, wherein the ring system

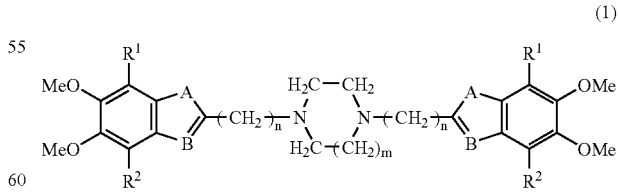

(1)

in formula (1) is selected from the group consisting of naphthalene, quinoline, quinazoline, benzimidazole, benzothiazole, benzoxazole, indole, benzothiophene and benzofuran.

7. The pharmaceutical composition of claim 4, comprising an effective amount of the compound of formula (1) for treating a disease selected from the group consisting of allergy, asthma, inflammation, rheumatism and asteriosclerosis.

8. A method for treating a disease selected from the group consisting of allergy, asthma, inflammation, rheumatism and asteriosclerosis, which comprises administering to a patient in need thereof a cyclic diamine compound formula (1):

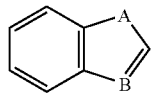

wherein $R^1$ and $R^2$ are individually a hydrogen atom or a methoxy group, provided $R^1$ is a methoxy group when $R^2$ is a hydrogen atom, or $R^1$ is a hydrogen atom when $R^2$ is a methoxy group; A is an oxygen atom, a sulfur atom, CH=CH, CH=N or $NR^3$, in which $R^3$ is a hydrogen atom, or a lower alkyl, hydroxy lower alkyl, lower alkoxy lower alkyl, aryl or aryl lower alkyl group; B is a nitrogen atom, CH or $CR^4$, in which $R^4$ is a hydrogen atom, or a lower alkyl, hydroxy lower alkyl, lower alkoxy lower alkyl, aryl or aryl lower alkyl group; m is 1; and n is a number of 1 to 5, an acid-addition salt thereof, or a hydrate thereof.

9. The method of claim 8, wherein $R^3$ and $R^4$ are individually a hydrogen atom, $C_1$–$C_6$-alkyl group, hydroxy-$C_2$–$C_6$-alkyl group, $C_1$–$C_6$-alkoxy-$C_1$–$C_6$-alkyl group, $C_6$–$C_{10}$-aryl or $C_6$–$C_{10}$-aryl-$C_1$–$C_6$-alkyl group.

10. The method of claim 8, wherein the ring system

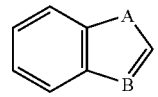

in formula (1) is selected from the group consisting of naphthalene, quinoline, quinazoline, benzimidazole, benzothiazole, benzoxazole, indole, benzothiophene and benzofuran.

* * * * *

UNITED STATES PATENT AND TRADEMARK OFFICE
CERTIFICATE OF CORRECTION

PATENT NO. : 7,135,473 B2  Page 1 of 2
APPLICATION NO. : 10/639457
DATED : November 14, 2006
INVENTOR(S) : Tatsuhiko Kodama et al.

It is certified that error appears in the above-identified patent and that said Letters Patent is hereby corrected as shown below:

Column 51, line 66, "m is 1 or 2" should read --m is 1.--

Column 52, line 41, "m is 1 or 2" should read --m is 1--.

line 55, " 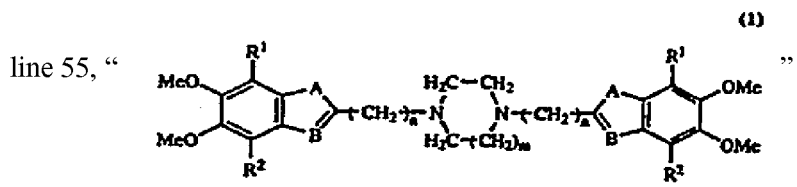 "

should read -- 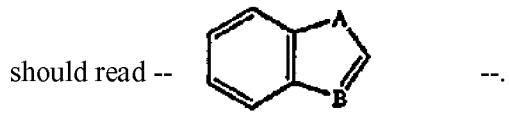 --.

Column 53, lines 2 and 3, "asteriosclerosis" should read --arteriosclerosis--.

line 6, "asteriosclerosis" should read --arteriosclerosis--.

Column 53, line 10, " 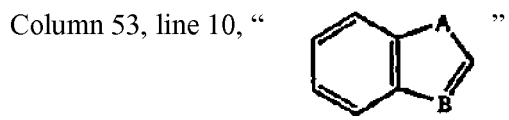 "

UNITED STATES PATENT AND TRADEMARK OFFICE
CERTIFICATE OF CORRECTION

PATENT NO.       : 7,135,473 B2  
APPLICATION NO.  : 10/639457  
DATED            : November 14, 2006  
INVENTOR(S)      : Tatsuhiko Kodama et al.

It is certified that error appears in the above-identified patent and that said Letters Patent is hereby corrected as shown below:

should read --
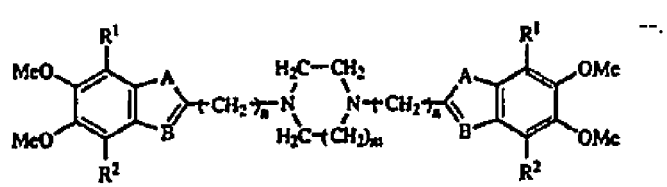
--.

Signed and Sealed this

Twenty-seventh Day of February, 2007

JON W. DUDAS  
*Director of the United States Patent and Trademark Office*